United States Patent
Fialkov et al.

(10) Patent No.: US 11,871,940 B2
(45) Date of Patent: Jan. 16, 2024

(54) CARTILAGE SLICING APPARATUS AND METHODS THEREFOR

(71) Applicant: Sunnybrook Research Institute, Toronto (CA)

(72) Inventors: Jeffrey Allan Fialkov, Toronto (CA); Harry Easton, Unionville (CA); Tara Lynn Teshima, Toronto (CA)

(73) Assignee: Sunnybrook Research Institute, Toronto (CA)

( * ) Notice: Subject to any disclaimer, the term of this patent is extended or adjusted under 35 U.S.C. 154(b) by 407 days.

(21) Appl. No.: 17/296,952

(22) PCT Filed: Nov. 26, 2019

(86) PCT No.: PCT/CA2019/051689
§ 371 (c)(1),
(2) Date: May 25, 2021

(87) PCT Pub. No.: WO2020/107106
PCT Pub. Date: Jun. 4, 2020

(65) Prior Publication Data
US 2022/0022892 A1   Jan. 27, 2022

Related U.S. Application Data

(60) Provisional application No. 62/771,742, filed on Nov. 27, 2018.

(51) Int. Cl.
*A61B 17/16* (2006.01)
*A61F 2/30* (2006.01)
(Continued)

(52) U.S. Cl.
CPC ...... *A61B 17/1635* (2013.01); *A61F 2/30756* (2013.01); *A61F 2/4618* (2013.01);
(Continued)

(58) Field of Classification Search
CPC ....... A61B 17/1635; A61B 2017/00969; A61F 2/4644; A61F 2002/3096; A61F 2002/30756; B26D 7/0616
See application file for complete search history.

(56) References Cited

U.S. PATENT DOCUMENTS

| 3,799,029 A | 3/1974 | Cole et al. |
| 5,461,953 A | 10/1995 | McCormick |

(Continued)

FOREIGN PATENT DOCUMENTS

| CN | 205626034 U | 10/2016 |
| CN | 108403183 A | 8/2018 |

(Continued)

OTHER PUBLICATIONS

"Desktop Cigar Cutter Mesa Fina Madera Oak Gold" Product Page, Cuben Crafters Cigars, accessed Feb. 9, 2017, at <https://cubancrafters.com/desktop-cigar-cutter-mesa-fina-madera-oak-gold/>.

(Continued)

*Primary Examiner* — Anu Ramana
(74) *Attorney, Agent, or Firm* — BERESKIN & PARR LLP/ S.E.N.C.R.L., s.r.l.; Nicholas Aitken

(57) ABSTRACT

An apparatus for slicing a cartilage sample includes a rear cartilage support cup, a cartilage clamp, a front cartilage support, a cartilage receiving region, and a cartilage cutting element. The cartilage clamp has first and second clamp members spaced apart from and aligned in a clamping direction transverse to a longitudinal axis. The cartilage receiving region is bounded by the first and second clamp members, the front cartilage support, and the rear cartilage support cup. The cartilage cutting element is spaced rearwardly from the front cartilage support by a cartilage slice thickness, the cartilage cutting element being movable (Continued)

across the cartilage receiving region in a cutting direction transverse to the longitudinal axis.

20 Claims, 19 Drawing Sheets

(51) Int. Cl.
*A61F 2/46* (2006.01)
*A61B 17/00* (2006.01)

(52) U.S. Cl.
CPC ............ *A61B 2017/00969* (2013.01); *A61F 2002/30764* (2013.01)

(56) References Cited

U.S. PATENT DOCUMENTS

| | | | |
|---|---|---|---|
| 5,571,131 A | 11/1996 | Ek et al. | |
| 5,785,714 A | 7/1998 | Morgan et al. | |
| 5,885,293 A | 3/1999 | McDevitt | |
| 5,906,148 A | 5/1999 | Aihara et al. | |
| 5,921,987 A | 7/1999 | Stone | |
| 6,962,592 B2* | 11/2005 | Gatturna | A61F 2/4644 606/184 |
| 7,780,668 B2 | 8/2010 | Steiner et al. | |
| 8,127,646 B2 | 3/2012 | Couvillion et al. | |
| 8,317,793 B2 | 11/2012 | Gil et al. | |
| 8,535,315 B2 | 9/2013 | Wong et al. | |
| 10,046,090 B2* | 8/2018 | Burden, Jr. | A61L 27/3691 |
| 10,182,925 B2* | 1/2019 | Ergun | A61B 17/1635 |
| 11,109,888 B1* | 9/2021 | Zahid | A61B 17/322 |
| 2002/0157676 A1 | 10/2002 | Schmieding | |
| 2006/0086221 A1 | 4/2006 | Kong et al. | |
| 2007/0135917 A1 | 6/2007 | Malinin | |
| 2008/0022831 A1 | 1/2008 | Watanabe et al. | |
| 2009/0192516 A1 | 7/2009 | Tallarida et al. | |
| 2009/0209962 A1 | 8/2009 | Jamali | |
| 2010/0268238 A1 | 10/2010 | Sikora et al. | |
| 2011/0165535 A1 | 7/2011 | Berger et al. | |
| 2012/0283793 A1 | 11/2012 | Burroughs, III | |
| 2014/0236306 A1 | 8/2014 | Karnes et al. | |
| 2014/0257299 A1 | 9/2014 | Berelsman et al. | |
| 2016/0081700 A1 | 3/2016 | Karnes et al. | |
| 2016/0120560 A1 | 5/2016 | Burroughs, III | |
| 2016/0166263 A1 | 6/2016 | Sauer | |
| 2018/0147072 A1 | 5/2018 | Ergun | |

FOREIGN PATENT DOCUMENTS

| | | |
|---|---|---|
| DE | 202013102433 U1 | 8/2013 |
| DE | 102013221060 B4 | 12/2016 |
| EP | 824893 A2 | 2/1998 |
| WO | 2003051210 A2 | 6/2003 |

OTHER PUBLICATIONS

"Costal Cartilage Graft Cutter" Product Page, Anthony Products, Inc, accessed Feb. 9, 2017 at <http://www.anthonyproducts.com/store/p-1071-costal-cartilage-graft-cutter.aspx%20(with%20video)>.

Foulad et al., "Practical Device for Precise Cutting of Costal Cartilage Grafts to Uniform Thickness", Arch Facial Plast Surg. Jul.-Aug. 2011; 13(4): 259-265.

Lopez, et al., "Analysis of the Physical Properties of Costal Cartilage in a Porcine Model", Arch Facial Plast Surg. Jan.-Feb. 2007;9(1):35-39.

International Search Report and Written Opinion, dated Feb. 24, 2020, International Application No. PCT/CA2019/051689 (7 pages).

Teshima et al., "Transverse Slicing of the Sixth-Seventh Costal Cartilaginous Junction: A Novel Technique to Prevent Warping in Nasal Surgery", J Craniofac Surg. Jan. 2016;27(1):e50-e55.

Stewart et al., "Transverse Slicing of the Sixth-Seventh Costal Cartilaginous Junction: A Novel Technique to Prevent Warping in Nasal Surgery" Presentation Slides, Surgery, University of Toronto (16 pages).

English Translation of Abstract of CN108403183, published Aug. 17, 2018.

English Translation of Abstract of DE102013221060, published Dec. 22, 2016.

English Translation of Abstract of CN205626034, published Oct. 10, 2016.

English Translation of Abstract of DE202013102433, published Aug. 8, 2013.

\* cited by examiner

US 11,871,940 B2

CARTILAGE SLICING APPARATUS AND METHODS THEREFOR

CROSS-REFERENCE TO RELATED APPLICATIONS

The present application is a national phase entry application of Patent Cooperation Treaty Application No. PCT/CA2019/051689, filed Nov. 26, 2019, which claims the benefit of priority from U.S. provisional patent application No. 62/771,742 filed Nov. 27, 2018, the contents of each of which are incorporated herein by reference in their entirety.

FIELD

This disclosure relates to the field of cartilage slicing apparatus and methods therefor.

INTRODUCTION

Costal cartilage is an important reconstructive tissue for correcting nasal deformities. In many cases, costal cartilage may be the graft of choice for nasal reconstructive and cosmetic surgery when septum cartilage is unavailable. In practice, a cartilage sample of costal cartilage must be cut into thin slices for use in such surgical procedures.

DRAWINGS

SUMMARY

Figure 1:
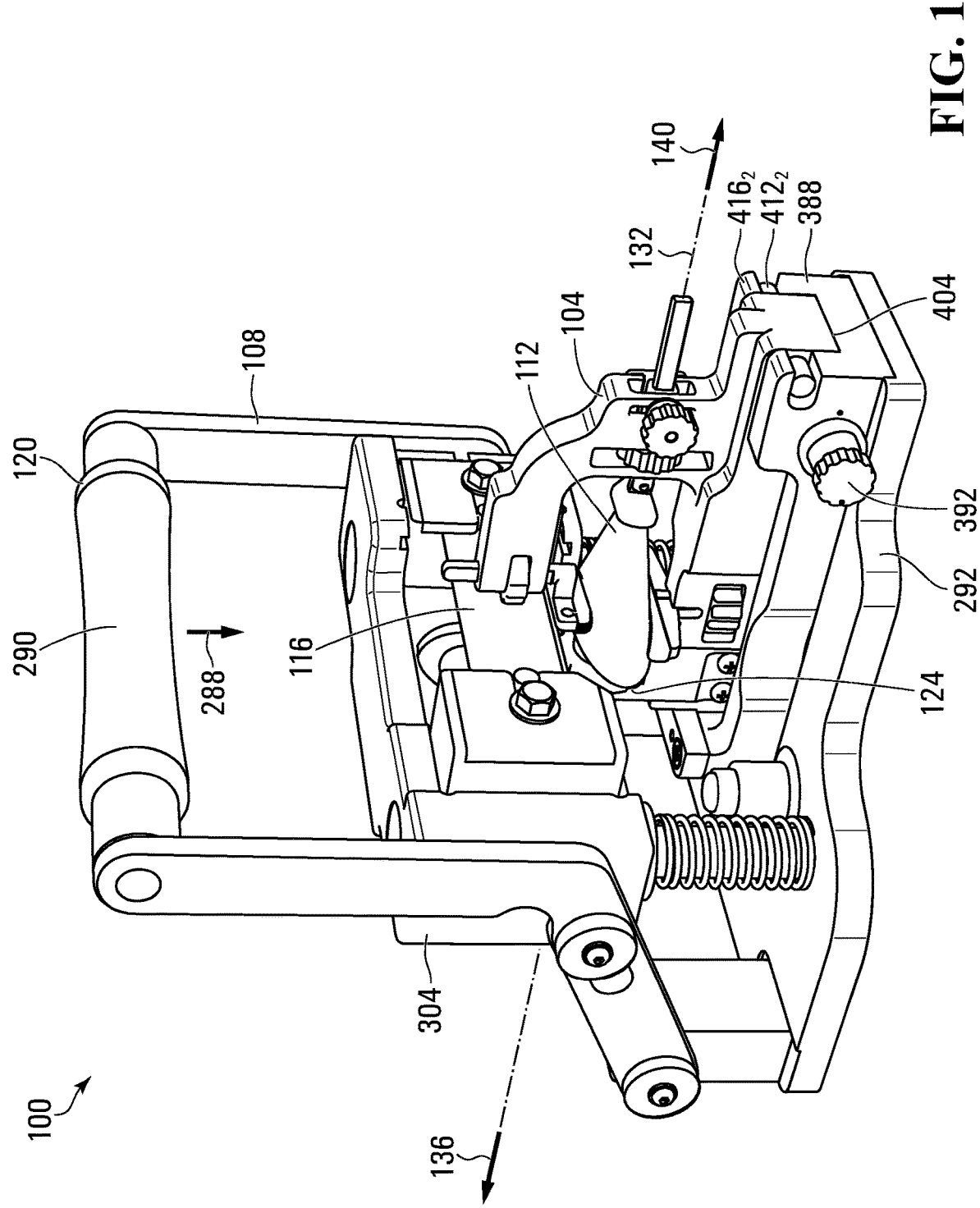
FIG. 1 is a front perspective view of a cartilage slicing apparatus, in accordance with an embodiment.
Figure 2:
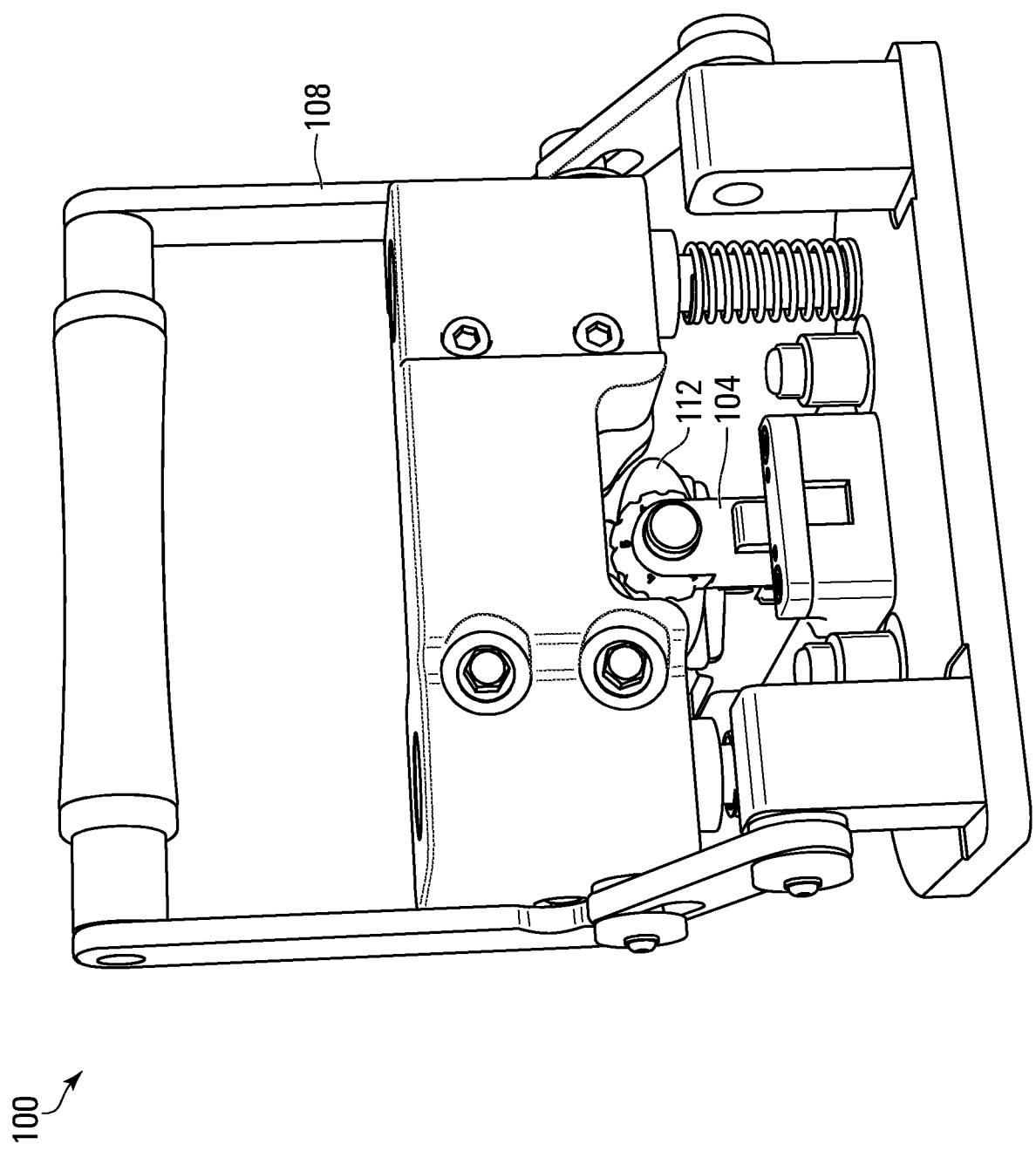
FIG. 2 is a rear perspective view of the cartilage slicing apparatus of FIG. 1.
Figure 3:
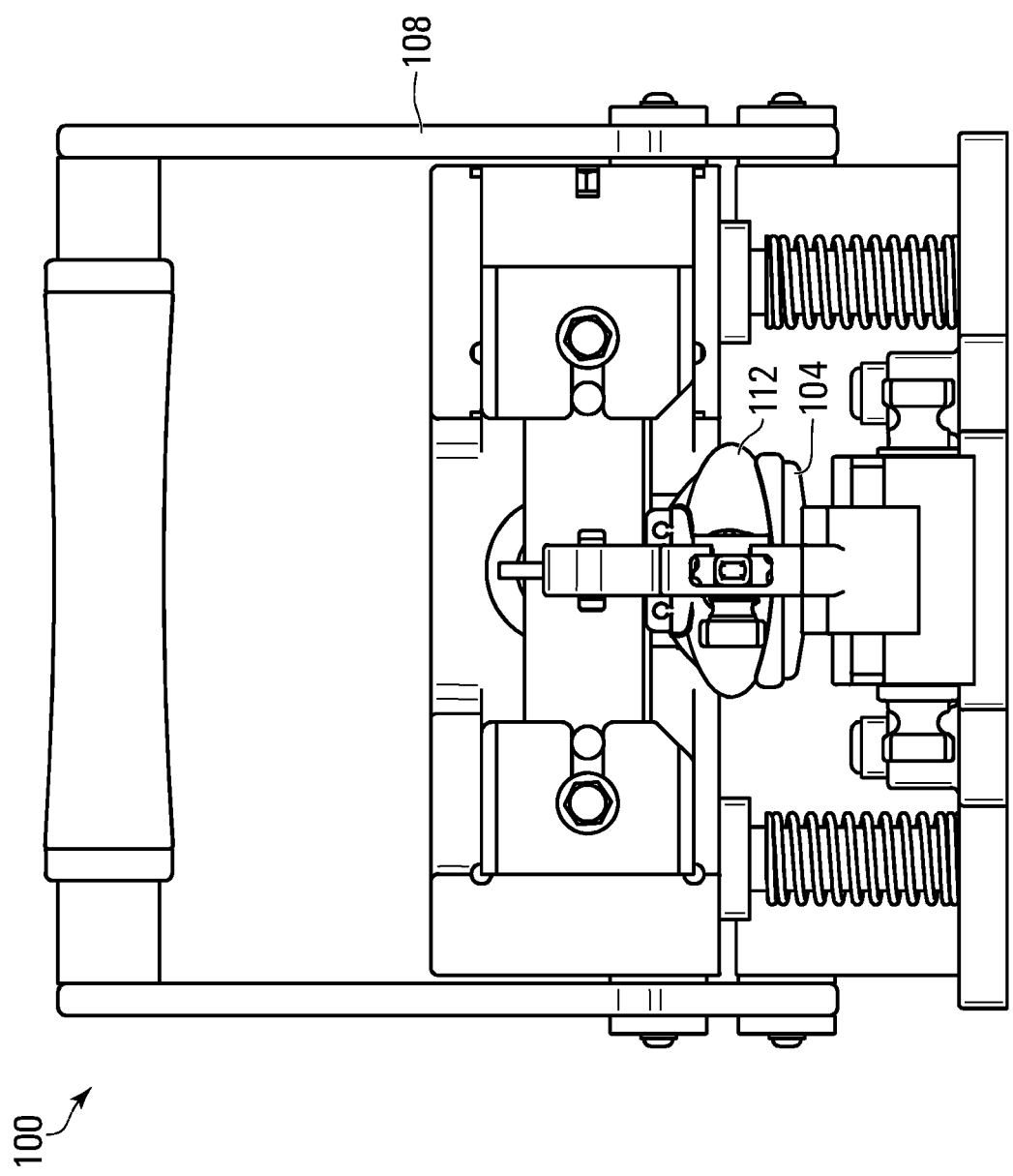
FIG. 3 is a rear elevation view of the cartilage slicing apparatus of FIG. 1.
Figure 4:
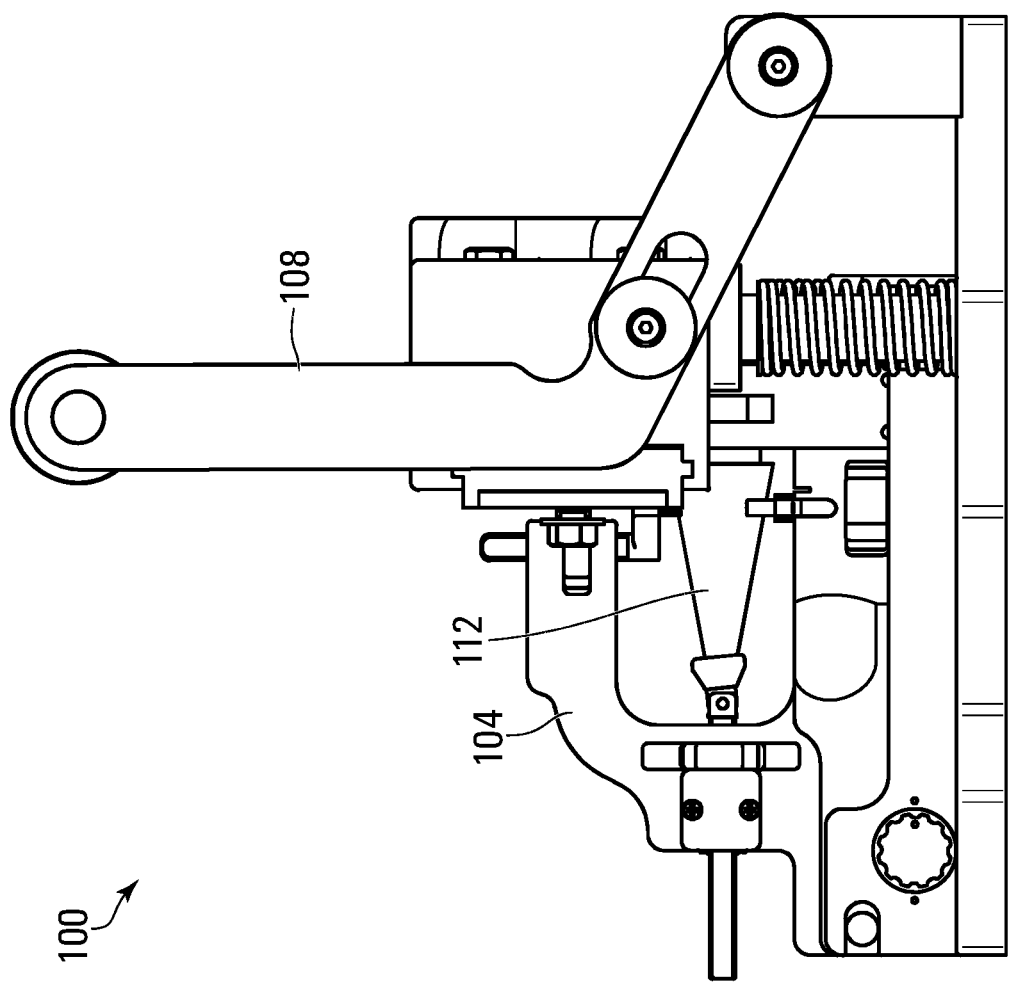
FIG. 4 is a right side elevation view of the cartilage slicing apparatus of FIG. 1.

In one aspect, an apparatus for slicing a cartilage sample is provided. The apparatus has a longitudinal axis extending in forward and rearward directions. The apparatus may include a rear cartilage support cup, a cartilage clamp positioned forward of the rear cartilage support cup, a front cartilage support positioned forward of the cartilage clamp, and a cartilage cutting element positioned forward of the cartilage clamp. The cartilage clamp may have first and second clamp members. The first clamp member may be spaced apart from and aligned with the second clamp member in a clamping direction transverse to the longitudinal axis. At least one of the first and second clamp members being movable parallel to the clamping direction. A cartilage receiving region may be bounded by the first and second clamp members, the front cartilage support, and the rear cartilage support cup. The cartilage cutting element may be spaced rearwardly from the front cartilage support by a cartilage slice thickness. The cartilage cutting element may be movable across the cartilage receiving region in a cutting direction transverse to the longitudinal axis.

In another aspect, a method of cutting a cartilage sample is provided. The method may include moving a front cartilage support longitudinally relative to a cartilage cutting element to define a slice thickness, the slice thickness measured in a forward direction; immobilizing the cartilage sample by engaging the cartilage sample with a transverse cartilage clamp, a rear cartilage support cup, and the front cartilage support; and cutting, with the cartilage cutting element, in a cutting direction that is transverse to the forward direction, a cartilage slice of the immobilized cartilage sample, the cartilage slice having a front end in contact with the front cartilage support and having the slice thickness.

DESCRIPTION OF VARIOUS EMBODIMENTS

Numerous embodiments are described in this application, and are presented for illustrative purposes only. The described embodiments are not intended to be limiting in any sense. The invention is widely applicable to numerous embodiments, as is readily apparent from the disclosure herein. Those skilled in the art will recognize that the present invention may be practiced with modification and alteration without departing from the teachings disclosed herein. Although particular features of the present invention may be described with reference to one or more particular embodiments or figures, it should be understood that such features are not limited to usage in the one or more particular embodiments or figures with reference to which they are described.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more parts are said to be "coupled", "connected", "attached", "joined", "affixed", or "fastened" where the parts are joined or operate together either directly or indirectly (i.e., through one or more intermediate parts), so long as a link occurs. As used herein and in the claims, two or more parts are said to be "directly coupled", "directly connected", "directly attached", "directly joined", "directly affixed", or "directly fastened" where the parts are connected in physical contact with each other. As used herein, two or more parts are said to be "rigidly coupled", "rigidly connected", "rigidly attached", "rigidly joined", "rigidly affixed", or "rigidly fastened" where the parts are coupled so as to move as one while maintaining a constant orientation relative to each other. None of the terms "coupled", "connected", "attached", "joined", "affixed", and "fastened" distinguish the manner in which two or more parts are joined together.

Further, although method steps may be described (in the disclosure and/or in the claims) in a sequential order, such methods may be configured to work in alternate orders. In other words, any sequence or order of steps that may be described does not necessarily indicate a requirement that the steps be performed in that order. The steps of methods described herein may be performed in any order that is practical. Further, some steps may be performed simultaneously.

As used herein and in the claims, a group of elements are said to 'collectively' perform an act where that act is performed by any one of the elements in the group, or performed cooperatively by two or more (or all) elements in the group.

As used herein and in the claims, a first element is said to be "received" in a second element where at least a portion of the first element is received in the second element unless specifically stated otherwise.

Some elements herein may be identified by a part number, which is composed of a base number followed by an alphabetical or subscript-numerical suffix (e.g. 112*a*, or 112$_1$). Multiple elements herein may be identified by part numbers that share a base number in common and that differ by their suffixes (e.g. 112$_1$, 112$_2$, and 112$_3$). All elements with a common base number may be referred to collectively or generically using the base number without a suffix (e.g. 112).

Costal cartilage is an important reconstructive tool for correcting nasal deformity resulting from, for example cancer resection, trauma, and congenital deformities. It is also a valuable source of cartilage in secondary aesthetic rhinoplasty. Autologous costal cartilage is flexible, resilient, and provides adequate strength. However, the major drawback of the use of costal cartilage graft is its tendency to warp. Warping of costal cartilage can lead to functional airflow problems and cosmetic deformity requiring subsequent surgical correction and added cost. Warping and its consequent deformity can therefore significantly affect the quality of life of patients requiring nasal reconstruction. Unfortunately, there has been little advancement in the understanding and prevention of costal cartilage warping prior to this disclosure. To date, concentric carving has been the most recommended technique for the prevention of costal cartilage warping in the context of nasal reconstruction. However, concentric carving of costal cartilage requires grafts to be carved parallel to the long axis of the rib and from its centre, in order to yields grafts of adequate length for clinical use. This limits the amount of graft material available and, as concentric carving is technically challenging, renders the grafts tendency to warp unpredictable.

The sixth-seventh costal cartilaginous junction, or synchondrosis, is a unique anatomic structure in the thorax that extends from the sixth to the seventh cartilaginous rib just lateral to the costal margin. The sixth-seventh costochondral junction is of dimensions, that when sliced transversely (e.g. perpendicularly) to the long axis of the junction itself, yield long narrow grafts, ideal for clinical use. Embodiments herein relate to a cartilage slicing apparatus that may be used to cut a cartilage sample (e.g. from the sixth-seventh costal cartilaginous junction) into many transverse parallel slices, which exhibit reduced warping as compared with, e.g. concentric carving techniques. In some embodiments, the apparatus allows the cartilage sample to be selectively cut into slices of any desired thickness from among a range or selection of slice thicknesses. In this way, these cartilage slices (i.e. grafts) can be harvested in their final dimensions without having to breach the outer surface of the costochondral junction, thus maintaining a cross-sectional balance of forces, which may contribute to reduced warping. Multiple transverse slices may be obtained from a single cartilage sample giving an abundance of cartilage slices of various lengths and controlled thickness ideal for nasal reconstruction.

Reference is first made to FIGS. 1-4, which show a cartilage slicing apparatus 100. As shown, cartilage slicing apparatus 100 may include a cartilage carrier 104 and a cartilage cutting assembly 108. In use, cartilage carrier 104 may be used to immobilize a cartilage sample 112, and cartilage cutting assembly 108 may be used to cut transverse cartilage slices from the cartilage sample 112.

Figure 5:
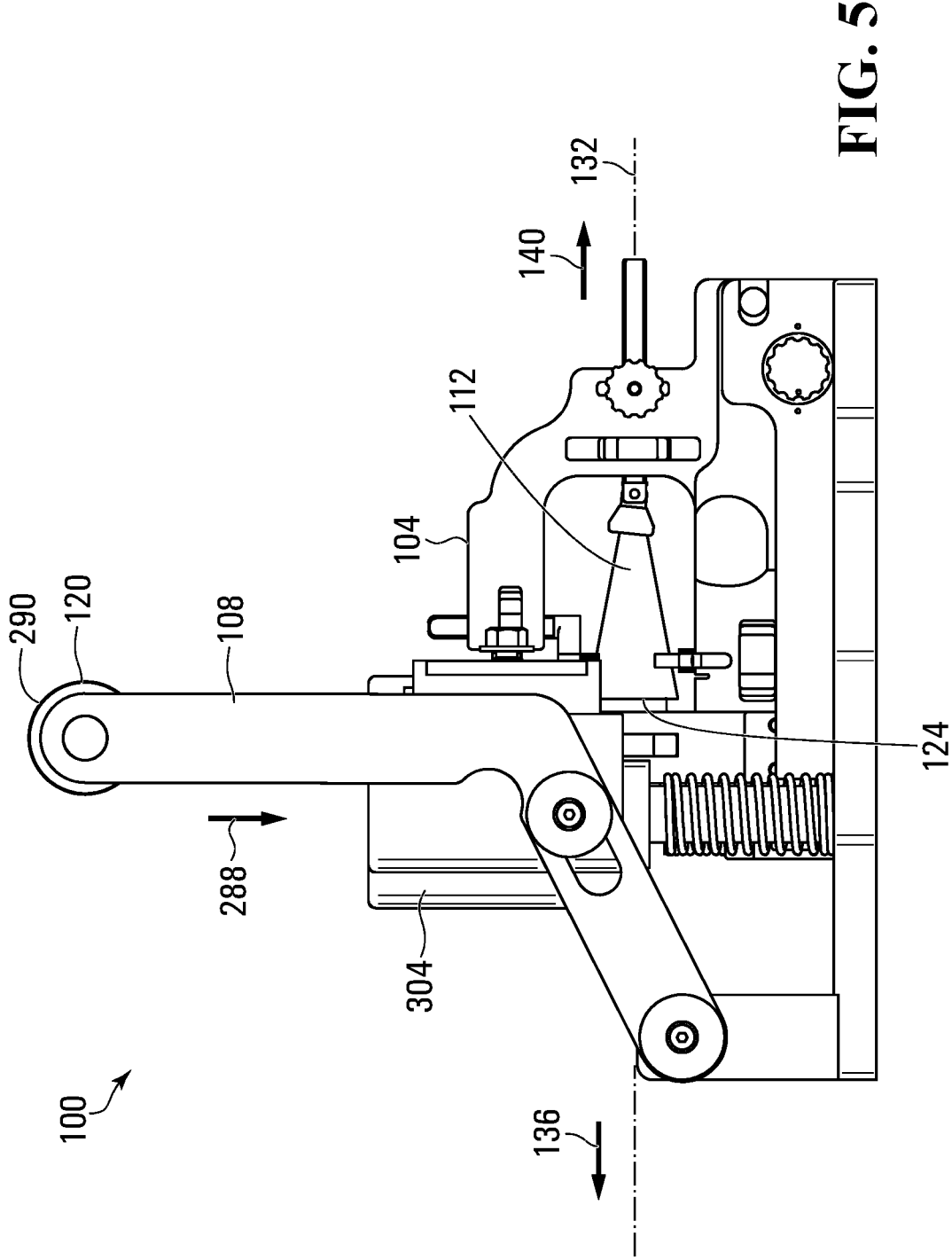
FIG. 5 is a left side elevation view of the cartilage slicing apparatus of FIG. 1 in a retracted position.
Figure 6:
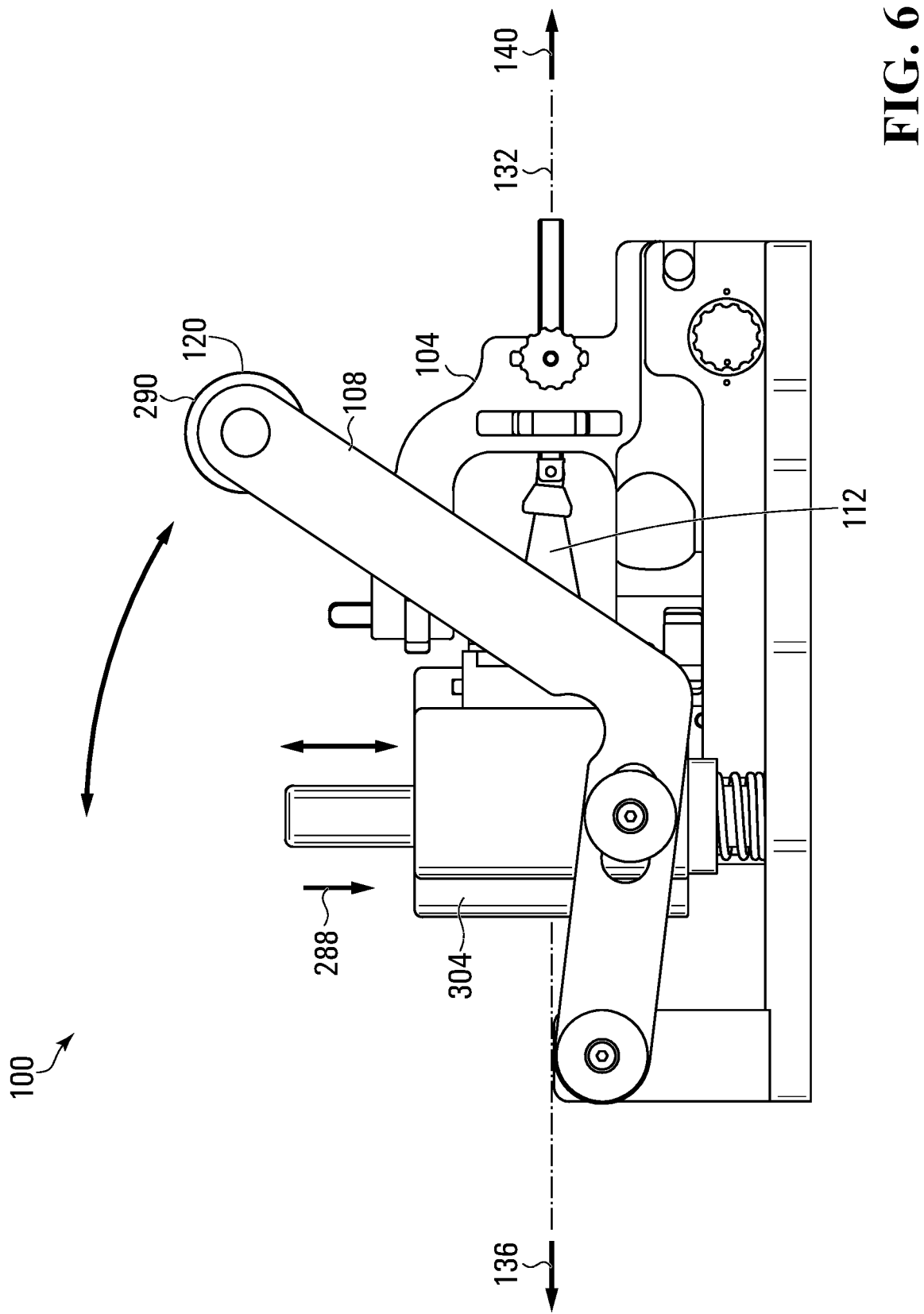
FIG. 6 is a left side elevation view of the cartilage slicing apparatus of FIG. 1 in an activated position.

As seen in FIGS. 1, 5, and 6, cartilage cutting assembly 108 may include a cartilage cutting element 116 and a cutting element actuator 120. Cutting element actuator 120 may be used to move cartilage cutting element 116 from a retracted position (FIG. 5) through the immobilized cartilage sample 112 to an activated position (FIG. 6) to cut a cartilage slice from a front end 124 (FIG. 2) of the cartilage sample 112. After cutting a cartilage slice, cartilage cutting assembly 108 and/or cartilage carrier 104 may be used to longitudinally advance the cartilage sample 112 relative to the cartilage cutting element 116 for cutting a subsequent cartilage slice. This may be repeated until the remaining cartilage sample 112 is too small for cartilage slicing apparatus 100 to cut another slice. In this way, cartilage slicing apparatus 100 may be able to produce many cartilage slices of controlled thickness from a cartilage sample 112 leaving little waste.

For the purposes of describing apparatus 100, and any subcomponents thereof, reference may be had to a longitudinal axis 132, as well as a forward direction 136, and a rearward direction 140. Forward and rearward directions 136 and 140 may be parallel to longitudinal axis 132 as shown. Longitudinal axis 132 is preferably perpendicular to the direction of gravity, but may be oriented differently. As used herein and in the claims, reference to "forwardly" or "forward of" mean in forward direction 136, reference to "rearwardly" or "rearward of" mean in rearward direction 140, and reference to longitudinally means in a direction parallel to longitudinal axis 132 (e.g. in forward or rearward directions 136, 140), unless specified otherwise. That is, references to directions and axes, such as "forward", "rearward", and "longitudinal", when used to describe subcomponents of apparatus 100, do so in reference to the global system of directions and axes of apparatus 100, unless specified otherwise. This is contrasted with the use of local directions and axes in which a direction such as 'forward' can mean a different direction for one subcomponent than for another subcomponent.

Two elements described as being one forwardly or rearwardly of the other; or forwardly, rearwardly, or longitudinally spaced apart, does not imply that the two elements are longitudinally aligned, unless specified otherwise. For example, the two elements may or may not be transversely offset or spaced apart. As used herein and in the claims, a first direction or axis is said to be "transverse" to a second direction or axis where the first direction or axis is perpendicular to, or within 45 degrees of perpendicular to, the second direction or axis, unless specified otherwise.

Figure 7:
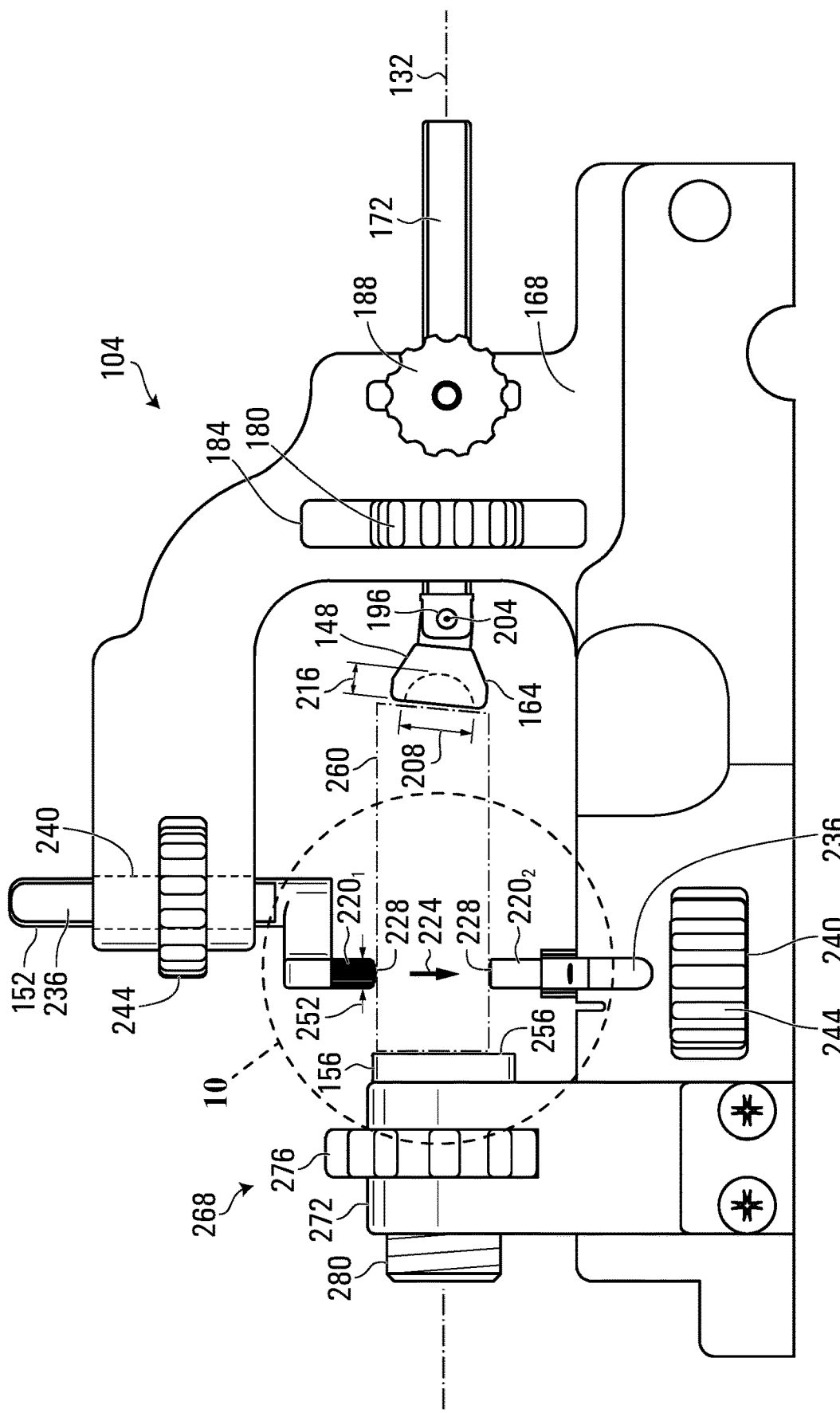
FIG. 7 is a cartilage carrier of the cartilage slicing apparatus of FIG. 1, in accordance with an embodiment.
Figure 8:
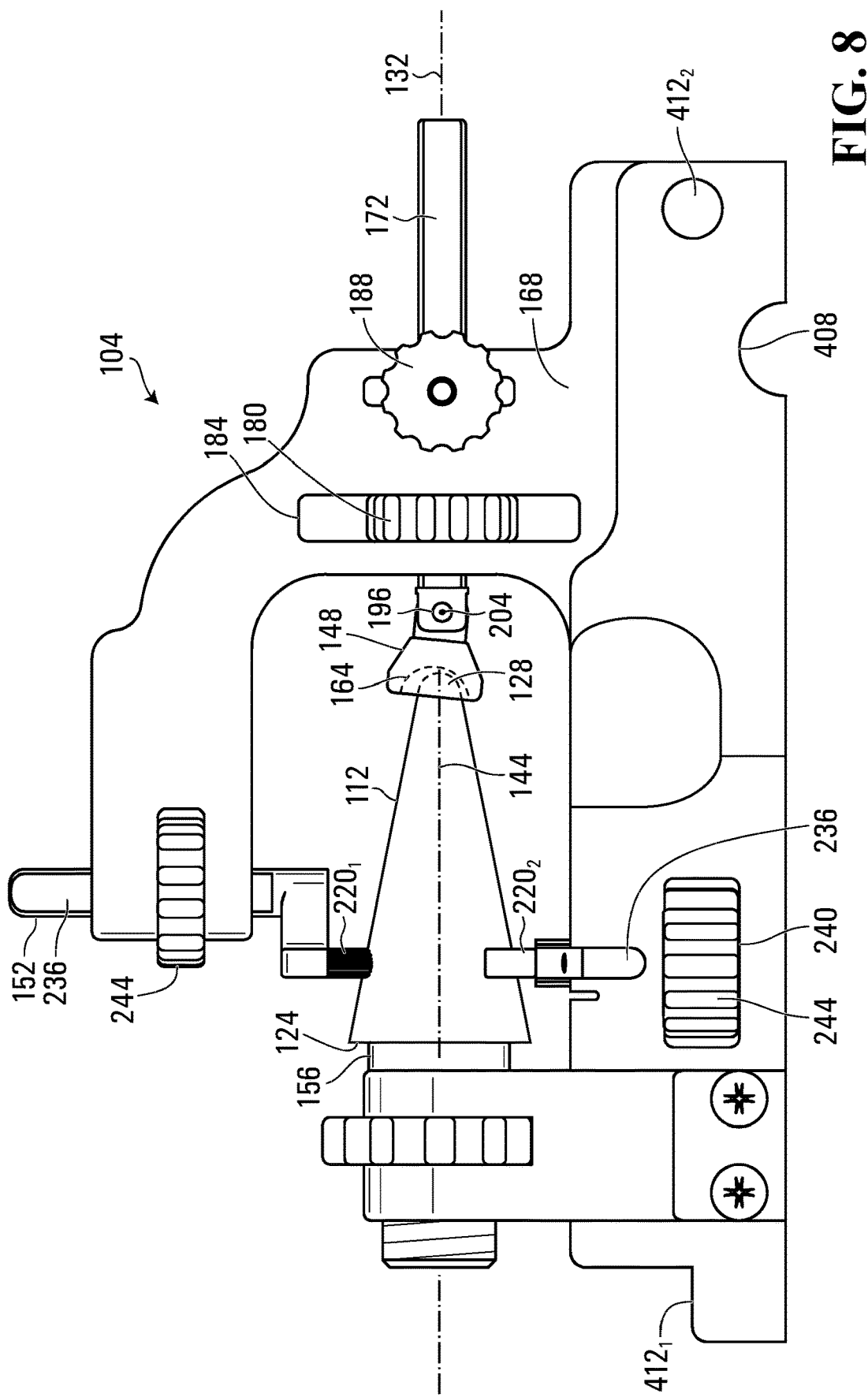
FIG. 8 is the cartilage carrier of FIG. 7 holding a cartilage sample.
Figure 9:
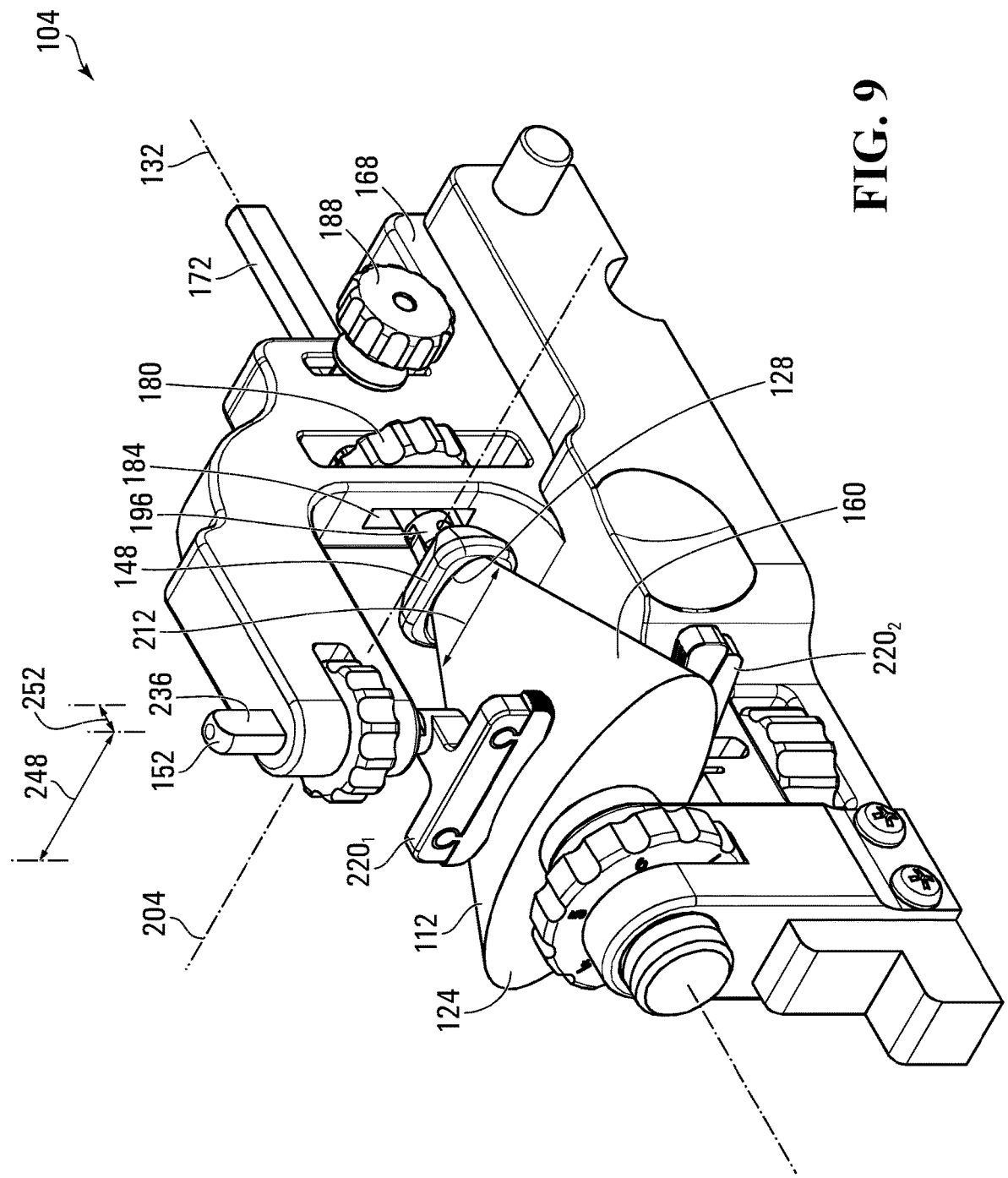
FIG. 9 is a perspective view of the cartilage carrier of FIG. 7 holding the cartilage sample.

Reference is now made to FIGS. 7-9. Cartilage carrier 104 may have any configuration suitable for immobilizing a cartilage sample 112 in an orientation that allows cartilage cutting assembly (FIG. 1) to cut transverse cartilage slices from sample 112. As shown, a cartilage sample 112 may have a long axis 144, which extends from a cartilage sample front end 124 to a cartilage sample rear end 128. Cartilage carrier 104 may hold cartilage sample 112 with cartilage sample long axis 144 oriented in any way relative to longitudinal axis 132. However, in the context of cutting cartilage sample 112 (e.g. costal cartilage, such as from the sixth-seventh costal cartilaginous junction) to produce cartilage slices best suited for nasal surgery, and with reduced warping, cartilage carrier 104 preferably holds cartilage sample 112 with cartilage sample long axis 144 oriented parallel to longitudinal axis 132.

Owing to the fact that cartilage sample 112 is a biological sample, cartilage sample 112 will typically have a cross-sectional shape (i.e. in a plane perpendicular to cartilage sample long axis 144) which varies along cartilage sample long axis 144 (and from sample to sample). In the illustrated example, cartilage sample 112 has a shape that approximates costal cartilage from the sixth-seventh costal cartilaginous junction (e.g. a conical or elliptic cone shape). As shown, cartilage sample 112 may taper in height and width from cartilage sample front end 124 to cartilage sample rear end 128. In many cases, cartilage sample rear end 128 may be formed roughly as a point as shown.

Still referring to FIGS. 7-9, cartilage carrier 104 may have a configuration that can immobilize an irregularly shaped cartilage sample 112 to the extent required to allow cartilage cutting assembly 108 (FIG. 1) to cleanly cut predicable cartilage slices from cartilage sample 112. As shown, cartilage carrier 104 may include a rear cartilage support 148, a cartilage clamp 152, and a front cartilage support 156. In use, rear cartilage support 148 may abut cartilage sample rear end 128 to inhibit rearward movement of cartilage sample 112 thereby providing rearward stability. Cartilage clamp 152 may be located forward of rear cartilage support 148 and abut cartilage sample mid-body 160 (i.e. a portion of cartilage sample 112 between its front and rear ends 124, 128) to inhibit movement of cartilage sample 112 in one or more transverse directions (i.e. direction(s) perpendicular to longitudinal axis 132) thereby providing transverse stability. Front cartilage support 156 may be located forward of cartilage clamp 152 and abut cartilage sample front end 124 to inhibit forward movement of cartilage sample 112 thereby providing forward stability. Accordingly, rear cartilage support 148, cartilage clamp 152, and front cartilage support 156 may collectively provide forward, rearward, and transverse stability to cartilage sample 112, whereby cartilage sample 112 may be effectively immobilized for cutting.

Rear cartilage support 148 may have any configuration suitable to provide rearward stability to cartilage sample 112. As shown, rear cartilage support 148 may include a cartilage contacting surface 164 that is generally forwardly facing, and that makes contact with cartilage sample rear end 128 to inhibit cartilage sample 112 from moving rearwardly. Cartilage contacting surface 164 may have any surface profile suitable to inhibit cartilage sample 112 from moving rearwardly. For example, depending on the shape of cartilage sample rear end 128, cartilage contacting surface 164 may be planar, convex, concave, or have another regular or irregular surface profile. In the illustrated example, cartilage contacting surface 164 is concave. In this case, rear cartilage support 148 may be referred to as a rear cartilage support cup 148. As shown, concave cartilage contacting surface 164 allows rear cartilage support 148 to receive cartilage sample rear end 128. This can allow rear cartilage support 148 to provide not only rearward stability to cartilage sample 112, but also some transverse stability to cartilage sample rear end 128. Depending on the configuration of cartilage clamp 152, cartilage sample rear end 128 may tend to rotate or deflect (e.g. slouch) downwards out of alignment with longitudinal axis 132. A concave cartilage contacting surface 164 can allow rear cartilage support 148 to hold cartilage sample rear end 128 in alignment with longitudinal axis 132.

Still referring to FIGS. 7-9, rear cartilage support 148 may movable longitudinally relative to front cartilage support 156, manually (i.e. by hand) or by powered means (e.g. using an electromechanical device, such as a motor or solenoid). For example, after a cartilage slice is removed, rear cartilage support 148 may be moved forwardly until the new cartilage sample front end 124 abuts front cartilage support 156, and longitudinal stability of cartilage sample 112 is restored for the next cutting operation. Rear cartilage support 148 may be longitudinally movable relative to front cartilage support 156 in any manner. In the illustrated example, rear cartilage support 148 is connected to cartilage carrier body 168 by an adjustment rod 172. Adjustment rod 172 is slideably positioned within a rear adjustment slot 176, and threadably engaged with a rear adjustment dial 180. In use, rear adjustment dial 180 may be manually user-rotated (i.e. by hand) to threadably move adjustment rod 172 longitudinally forwards or rearwards. In other embodiments, rear cartilage support 148 may be longitudinally movable by electromechanical means, such as in a motor driven assembly. For example, adjustment rod 172 or rear adjustment dial 180 may be rotated by a motor activated by a manually user-operable switch to move rear cartilage support 148 longitudinally relative to front cartilage support 156.

Still referring to FIGS. 7-9, the transverse position of rear cartilage support 148 may be fixed, or may be adjustable (e.g. relative to other components of cartilage carrier 104, such as cartilage clamp 152 and/or front cartilage support 156). In the latter case, the transverse position of rear cartilage support 148 may be adjusted to accommodate the shape of cartilage sample 112, such as to hold cartilage sample long axis 144 in alignment with longitudinal axis 132. This can provide a preferred orientation for cutting transverse cartilage slices from cartilage sample 112 for use as grafts in nasal surgery.

In some embodiments, rear cartilage support 148 may be movable in or more directions transverse to longitudinal axis 132. For example, rear cartilage support 148 may be movable vertically as shown, horizontally, or in another direction. Rear cartilage support 148 may be movable in a transverse direction in any manner. In the illustrated example, adjustment rod 172 extends within a rear transversely extending slot 184 that allows adjustment rod 172 to move transversely between the ends of the rear transverse slot 184. Cartilage carrier 104 may be configure to retain rear cartilage support 148 at a selected transverse position. This allows rear cartilage support 148 to maintain a transverse position against, e.g. gravity and/or forces exerted by cartilage sample 112. In the illustrated example, a rear adjustment lock 188 is movable between a locked position in which adjustment rod 172 is inhibited from moving transversely (e.g. vertically in the example shown) along rear transverse slot 184, and an unlocked position in which adjustment rod 172 is free to move along rear transverse slot 184.

In alternative embodiments, rear cartilage support 148 is not transversely movable. This may simplify the design of rear cartilage support 148, which may reduce manufacturing complexity and cost, and possibly improve reliability.

Still referring to FIGS. 7-9, alternatively or in addition to rear cartilage support 148 being movable in one or more transverse directions, rear cartilage support 148 may be rotatable such that cartilage contacting surface 164 can generally face in directions non-parallel to longitudinal axis 132. This can allow cartilage contacting surface 164 to be oriented in a direction that provides best support for cartilage sample rear end 128. For example, in the illustrated example, rear cartilage support 148 is angled slightly upwardly as compared to longitudinal axis 132. Rear cartilage support 148 may be rotatable about one of more rotation axes that are non-parallel to (e.g. transverse to) longitudinal axis 132. For example, rear cartilage support 148 may be coupled to cartilage carrier body 168 by way of a joint 196, such as a hinge as shown, ball joint, or flex-joint. In the illustrated example, hinge 196 joins cartilage carrier body 168 to rear adjustment rod 172, and allows rear cartilage support 148 to rotate about a rotation axis 204 that is transverse to longitudinal axis 132. For example, rotation axis 204 may be horizontal as shown, vertical, or another orientation transverse to longitudinal axis 132.

In alternative embodiments, rear cartilage support 148 is not rotatable. This may simplify the design of rear cartilage support 148, which may reduce manufacturing complexity and cost, and possibly improve reliability.

Rear cartilage contacting surface 164 may have any dimensions suitable to provide rearward stability (and transverse stability depending on the configuration) to cartilage sample rear end 128. For example, rear cartilage contacting surface 164 may have a height 208 (FIG. 7) of between 5 mm and 25 mm, a width 212 (FIG. 9) of between 5 mm and 25 mm, and if it is concave then a depth 216 (FIG. 7) of between 1 mm and 25 mm. Dimensions within these ranges may be best suited for stabilizing a cartilage sample 112. However, dimensions outside of these value ranges may be also be used to accommodate various applications.

Still referring to FIGS. 7-9, cartilage clamp 152 may have any configuration suitable to provide transverse stability, in one or more directions transverse to longitudinal axis 132, to cartilage sample 112. As shown, cartilage clamp 152 may include first and second transverse clamp members 2201 and 2202. First clamp member 2201 may be spaced apart from second clamp member 2202 in a clamping direction 224 (FIG. 7) that is transverse to (e.g. perpendicular to) longitudinal axis 132. Each clamp member 220 has a cartilage contacting surface 228 (FIG. 7), which may be referred to as a "clamp cartilage contacting surface". In use, cartilage sample mid-body 160 is located between clamp members 220, and cartilage contacting surface 228 contact cartilage sample mid-body 160 to provide transverse stability to cartilage sample 112 (e.g. to inhibit cartilage sample mid-body 160 from moving parallel to clamping direction 224).

Optionally, but preferably, clamp members 220 are aligned in the clamping direction 224 as shown. This allows clamp members 220 to provide reactionary forces to oppose the clamp forces each one applies to cartilage sample 112. If clamp members 220 were misaligned (e.g. longitudinally offset from each other), then the forces exerted by clamp members 220 upon cartilage sample 112 may urge cartilage sample 112 to rotate or twist. Still, there may be circumstances in which such rotation or twist may desirably help to align long axis 144 of an oddly shaped cartilage sample 112 with longitudinal axis 132.

Clamping direction 224 may be any direction transverse to longitudinal axis 132. For example, clamping direction 224 may be vertical (i.e. parallel to gravity) as shown, horizontal, or another transverse direction. An advantage to a vertical clamping direction 224 is that it may permit cartilage clamp 152 to better stabilize cartilage sample 112 against the force of gravity. For example, lower clamp member 2202 may oppose the force of gravity upon cartilage sample 112.

Still referring to FIGS. 7-9, one or more of clamp members 220 may be movable toward the other clamp member 220. This can allow clamp cartilage contacting surfaces 228 to bear onto cartilage sample 112. For example, one or both of clamp members 220 may be movable parallel to clamping direction 224. In the illustrated example, both of clamp members 220 are movable parallel to clamping direction 224 towards the other clamp member 220. This provides greater flexibility to cartilage clamp 152 to hold cartilage sample mid-body 160 at a transverse position (e.g. elevation, as shown) which best aligns cartilage sample long axis 144 with longitudinal axis 132.

A clamp member 220 may be movable toward the other clamp member 220 (e.g. parallel to clamping direction 224) in any manner that allows the transverse clamp gap 232 between the clamp members 220 to be adjusted to accommodate the shape of cartilage sample mid-body 160. For example, clamp member 220 may be manually movable (i.e. by hand, without power), or power-movable (e.g. by an electro-mechanical device, such as an electric motor or solenoid). In the illustrated embodiment, clamp members 2201 and 2202 are manually movable parallel to clamping direction 224. As shown, each clamp member 220 may be connected to cartilage carrier body 168 by way of an adjustment rod 236, which may be referred to as a "clamp adjustment rod". Each clamp adjustment rod 236 may be transversely movable (e.g. parallel to clamping direction 224 as shown) within a transversely extending adjustment slot 240 (FIG. 7) (e.g. aperture or bore), which may referred to as a "clamp adjustment slot". As shown, a clamp adjustment dial 244 may threadably engage each clamp adjustment rod 236. In use, clamp adjustment dial 244 may be manually user-rotated to threadably advance the connected clamp adjustment rod 236 transversely (e.g. parallel to clamping direction 224).

Clamp members 220 may have any dimensions suitable for providing transverse stability to cartilage sample 112. For example, clamp members 220 may have a transverse width 248 of between 3 mm and 50 mm, and a longitudinal depth 252 of between 1 mm and 20 mm. In some embodiment, clamp members 220 may have a shallow depth dimension 252 (e.g. between 1 mm and 5 mm). This can improve sample cutting efficiency, by reducing the minimum remaining cartilage sample length required to allow cartilage carrier 104 to hold the cartilage sample 112 during a cutting operation. For example, the minimum cartilage sample length may be defined by a longitudinal distance between rear cartilage support 148 and front cartilage support 156 when rear cartilage support 148 abuts cartilage clamp 152. A small clamp depth 252 may reduce this longitudinal dimension, and thereby allow more cartilage slices to be cut from a cartilage sample 112.

Figure 10:
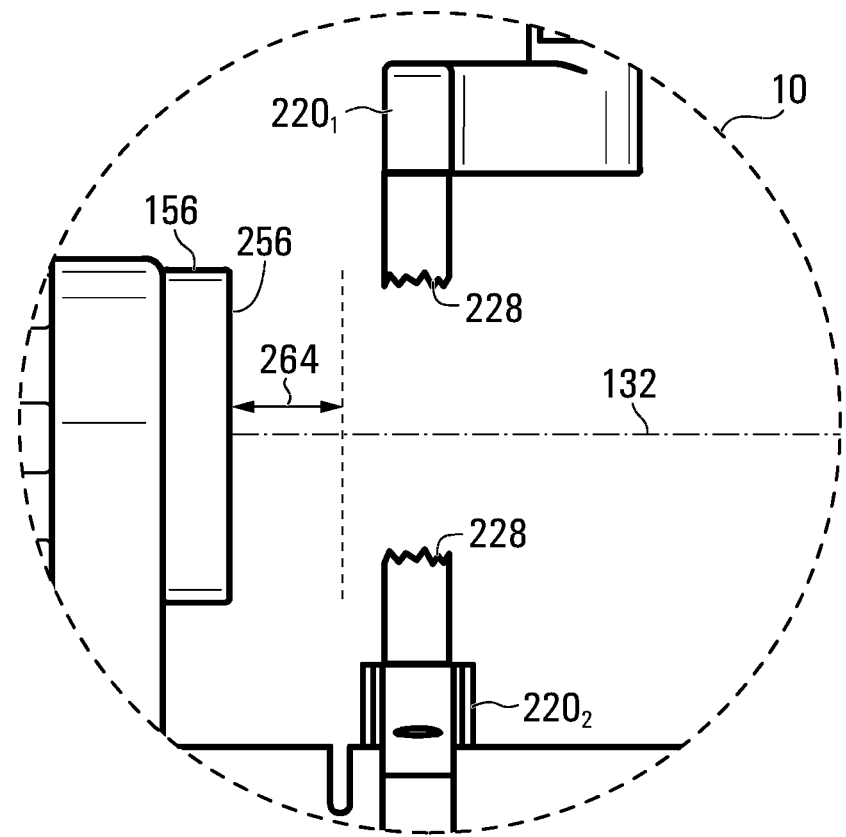
FIG. 10 is an enlargement of region 10 of FIG. 7.

Reference is now made to FIG. 10. In some embodiments, the cartilage contacting surface 228 of one or both of clamp members 220 may have a surface profile that allows cartilage clamp 152 to provide some longitudinal stability to cartilage sample 112 during cutting. For example, as cutting element 116 (FIG. 1) moves through cartilage sample 112, cartilage sample 112 may tend to longitudinally deform (e.g. pull rearwardly away from cutting element 116). This may produce a warped cartilage slice. Clamp cartilage contacting surface(s) 228 may help to longitudinally stabilize cartilage sample 112 (FIG. 1) at a location very close to the cut, which can mitigate cartilage sample deformation and cartilage slice warping. As shown, one or both cartilage contacting surfaces 228 may be transversely ridged (i.e. include ridges arranged in the longitudinal direction), allowing the cartilage contacting surface 228 to bite the cartilage sample 112 (FIG. 1) and provide longitudinal stability proximate the cutting zone.

In alternative embodiments, neither of clamp members 220 has a ridged cartilage contacting surface 228. This may simplify the design of clamp members 220, which may reduce manufacturing complexity and cost, and possibly improve reliability.

Referring back to FIGS. 7-9, front cartilage support 156 may have any configuration suitable to provide forward stability to cartilage sample 112. As shown, front cartilage support 156 may include a front cartilage contacting surface 256 (FIG. 7) that is generally rearward facing, and that makes contact with cartilage sample front end 124 to inhibit cartilage sample 112 from moving forwardly. As shown, front cartilage support 156 is located forwards of both cartilage clamp 152 and rear cartilage support 148.

Front cartilage support 156, cartilage clamp 152, and rear cartilage support 148 together bound a cartilage receiving region 260 (FIG. 7) (also referred to as a "cartilage receiving volume") where a cartilage sample 112 is located when immobilized by cartilage carrier 104. For example, cartilage receiving region 260 may extend forwardly to front cartilage contacting surface 256, rearwardly to rear cartilage contacting surface 164, and transversely to clamp cartilage contacting surfaces 228. During a cutting operation, cartilage cutting element 116 (FIG. 1) moves across cartilage receiving region 260 in a cutting direction transverse to longitudinal axis 132 to remove a cartilage slice from cartilage sample front end 124.

In some embodiments, front cartilage support 156 may be longitudinally aligned with rear cartilage support 148. That is, a line parallel to longitudinal axis 132 may intersect both of front cartilage support 156 (e.g. front cartilage contacting surface 256) and rear cartilage support 148 (e.g. rear cartilage contacting surface 164). This can allow front and rear cartilage supports 156, 148 to provide opposing forces upon a cartilage sample 112 for longitudinal stability. Still, in some cases the shape of cartilage sample 112 may be such that front and rear cartilage supports 156 and 148 are not longitudinally aligned (e.g. they are transversely offset). For example, rear cartilage support 148 may be transversely moved and/or rotated out of longitudinal alignment with front cartilage support 156 in order to make better contact with cartilage sample rear end 128.

Referring to FIGS. 1 and 10, the longitudinal distance between front cartilage support 156 (e.g. at least front cartilage contacting surface 256) and cartilage cutting element 116 in the activated position (FIG. 6) defines a cartilage slice thickness 264 (i.e. measured parallel to longitudinal axis 132). That is, when cartilage cutting assembly 108 is activated, the resulting cartilage slice will extend longitudinal from cartilage sample front end 124, which abuts front cartilage support 156, and a newly cut surface at the location of cartilage cutting element 116. Front cartilage support 156 and cartilage cutting element 116 may be longitudinally spaced apart in accordance with any cartilage slice thickness 264 suitable for an intended purpose. In the context of producing cartilage slices for use as grafts in nasal surgeries, cartilage slice thickness 264 may be between 0.1 mm and 10 mm. This allows cartilage slicing apparatus 100 to cut cartilage slices having clinically useful dimensions. In other embodiments, a cartilage slice thickness 264 outside this value range may be employed for use in other contexts.

The relative longitudinal positions of front cartilage support 156 and cartilage cutting element 116 may provide a fixed (i.e. non-adjustable) cartilage slice thickness 264, or an adjustable cartilage slice thickness 264. A fixed cartilage slice thickness 264 may provide better reliability, more accurate and precise cartilage slice thickness 264, and fewer moving parts leading to a simpler and less expensive design all else being equal. For example, a clinic may be equipped with several cartilage slicing apparatus 100 with each one set to a different, but fixed, cartilage slice thickness 264.

In the illustrated embodiment, the relative longitudinal position of front cartilage support 156 relative to cartilage cutting element 116 is adjustable to provide an adjustable cartilage slice thickness 264. This allows a single cartilage slicing apparatus 100 to produce cartilage slices of several different slice thickness (e.g. two or more discrete cartilage slice thickness, or any/every cartilage slice thickness within a range of cartilage slice thicknesses). As compared to having several cartilage slicing apparatus 100 with different but fixed cartilage slice thicknesses 264, an adjustable cartilage slice thickness 264 may reduce or eliminate the need to move a cartilage sample 112 between different cartilage slicing apparatus 100 in order to produce cartilage slices of different slice thicknesses from a single cartilage sample 112.

Figure 12:
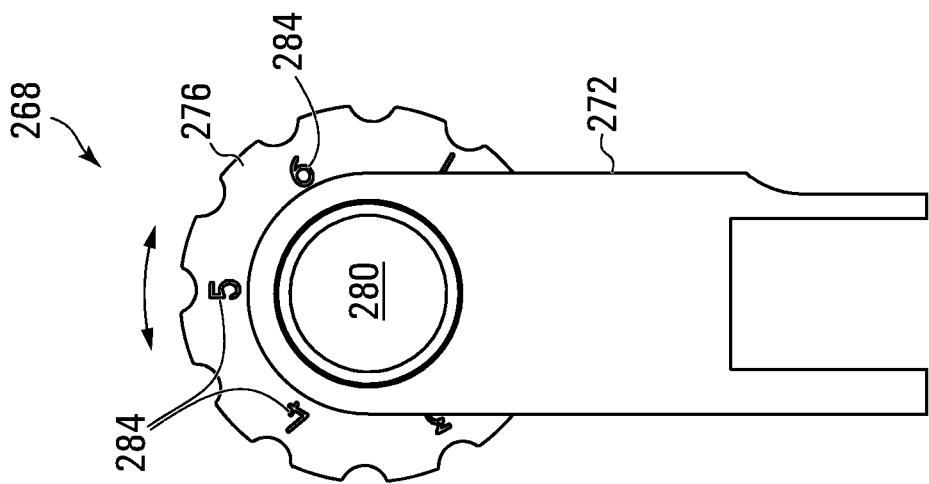
FIG. 12 is a front elevation view of the slice thickness adjuster of FIG. 11.
Figure 11:
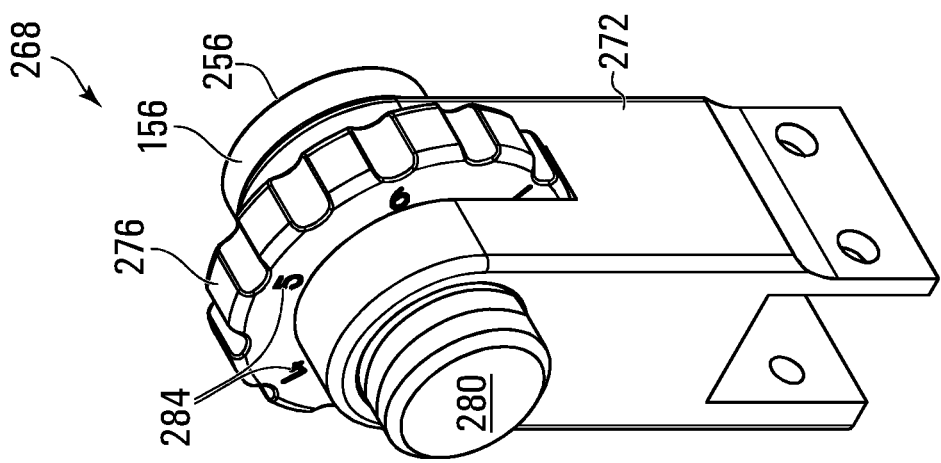
FIG. 11 is a front perspective view of a slice thickness adjuster of the cartilage slicing apparatus of FIG. 1, in accordance with an embodiment.

Referring to FIGS. 7, 11, and 12, front cartilage support 156 may be selectively movable longitudinally by a slice thickness adjuster 268. Slice thickness adjuster 268 may have any configuration that can be user-manipulated (e.g. user-controlled) to move front cartilage support 156 longitudinally (e.g. forwards or rearwards) relative to cartilage cutting element 116 (FIG. 1) to adjust cartilage slice thickness 264 (FIG. 10). For example, manipulating slice thickness adjuster 268 may move front cartilage support 156 manually (i.e. by human motive force, without electrical power), or by powered-means (e.g. by activating an electromechanical device, such as a motor or solenoid).

In the illustrated embodiment, slice thickness adjuster 268 is shown including a body 272, front cartilage support 156, and a slice thickness selector 276. In this example, adjuster body 272 may be rigidly connected to cartilage carrier body 168, and manipulating slice thickness adjuster 268 may move front cartilage support 156 longitudinally relative to adjuster body 272 (and therefore relative to cartilage carrier body 168). As shown, front cartilage support 156 may be threadably coupled to slice thickness selector 276 by way of a front adjustment rod 280. In use, slice thickness selector 276 may be manually user actuated (e.g. rotated) to longitudinally advance front cartilage support 156 relative to adjuster body 272.

Alternatively or in addition to allowing front cartilage support 156 to move longitudinally relative to cartilage carrier body 168, adjuster body 272 may be movably connected to cartilage carrier body 168 so that adjuster body 272 can be selectively moved longitudinally relative to cartilage carrier body 168.

Still referring to FIGS. 7, 11, and 12, in some embodiments slice thickness adjuster 268 may include one or more visual indicia 284 (also referred to as slice thickness visual indicia) that provide an indication of the cartilage slice thickness 264 (FIG. 7) provided by the current longitudinal position of front cartilage support 156 relative to cartilage cutting element 116 (FIG. 1). For example, visual indicia 284 may include actual measurement values (e.g. numbers which correspond to the cartilage slice thickness 264 (FIG. 10) in a particular measurement unit, such as millimeters or thousands of an inch), coded symbols (e.g. a progression of letters and/or numbers), and/or coded colors (a progression or spectrum of colors). In the illustrated embodiment, visual indicia 284 include actual measurement values representing the cartilage slice thickness 264 (FIG. 10) in millimeters.

In alternative embodiments, slice thickness adjuster 268 may not include visual indicium 284. This may simplify the design of slice thickness adjuster 268, which may reduce manufacturing complexity and cost.

Figure 13:
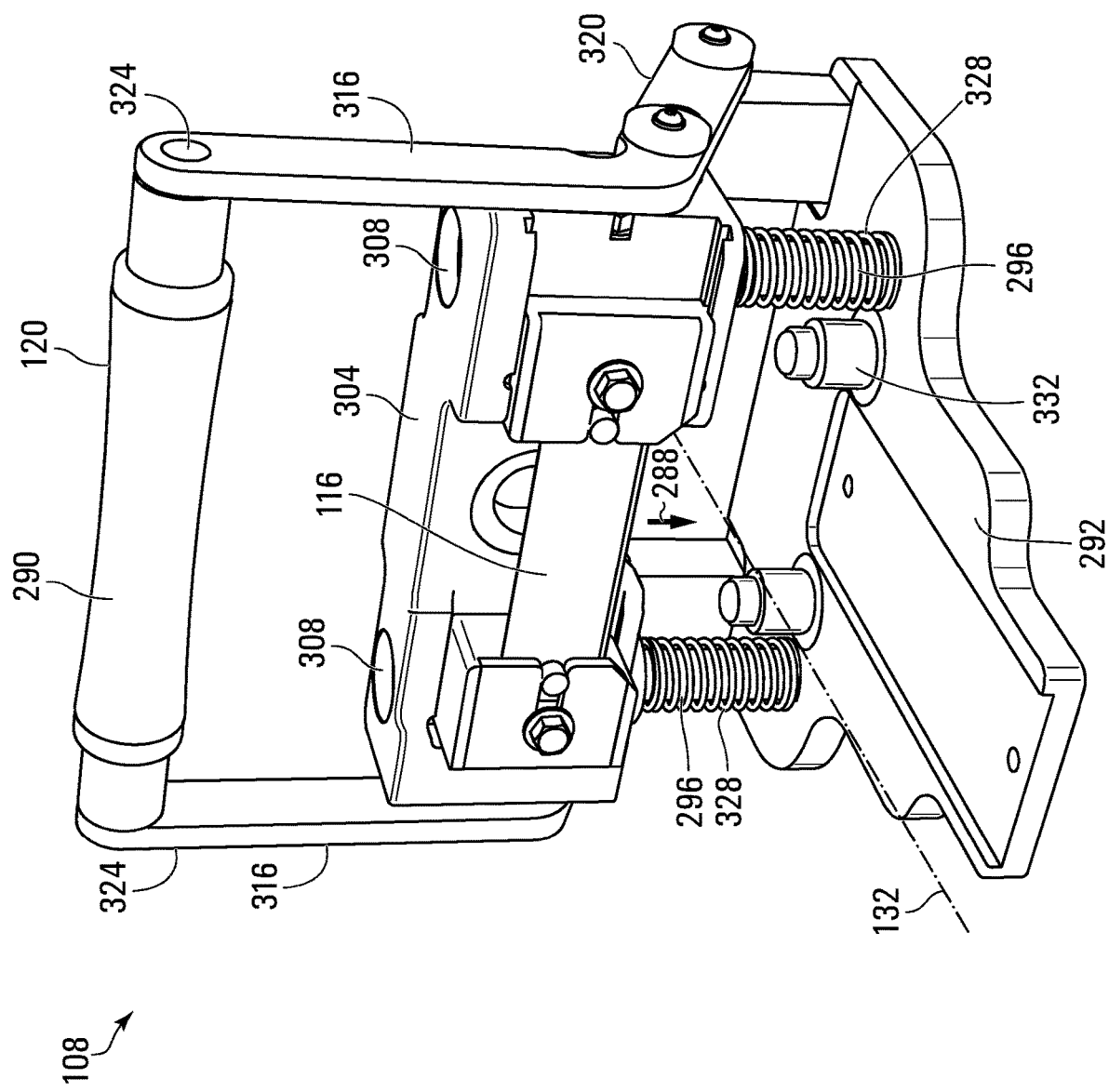
FIG. 13 is a perspective view of a cartilage cutting assembly on a base of the cartilage slicing apparatus of FIG. 1, in accordance with an embodiment.
Figure 14:
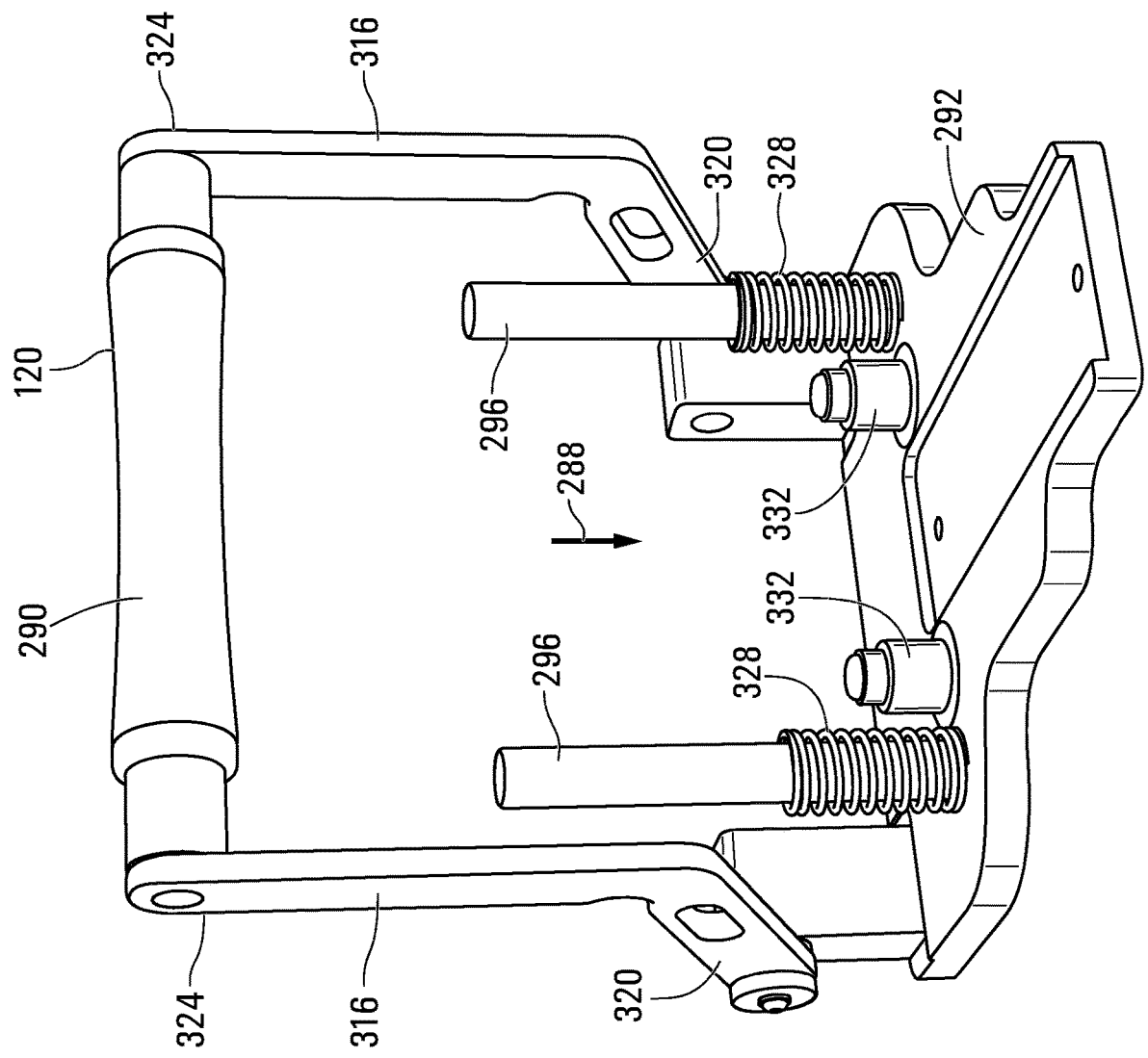
FIG. 14 is a perspective view of the cartilage cutting assembly of FIG. 13, with a cutting block removed.

Reference is now made to FIGS. 1, 13, and 14. Cartilage cutting assembly 108 may include any cutting element actuator 120 suitable to cut cartilage slices from a cartilage sample 112 immobilized by cartilage carrier 104. For example, cutting element actuator 120 may be user-activated to move cartilage cutting element 116 across cartilage sample 112 (i.e. across cartilage receiving region 260 (FIG. 7)) in a cutting direction 288 transverse to longitudinal axis 132. In preferred embodiments, cutting element actuator 120 moves cartilage cutting element 116 in a linear path parallel to cutting direction 288. This allows cartilage cutting assembly 108 to cut cartilage slices with planar longitudinal end faces, which are preferred for use as grafts in nasal surgery. In alternative embodiments, cutting element actuator 120 may move cartilage cutting element in a non-linear path (e.g. curved path, such as an arcuate or bent path) to produce curved cartilage slices for other applications.

Cutting element actuator 120 may be manually user activated (i.e. operate by human force, without any electrical power) or power activated (e.g. include an electromechanical device, such as a motor or solenoid). In the illustrated embodiment, cutting element actuator 120 includes a manually user-operable handle 290. As shown in FIGS. 5-6, a user may manipulate (e.g. pull) handle 290 to move cartilage cutting element (FIG. 1) from the retracted position (FIG. 5) across cartilage sample 112 to the activated position (FIG. 6).

Returning to FIG. 13, cutting element actuator 120 may be connected to cartilage cutting element 116 in any manner that allows cutting element actuator 120, when activated, to move cartilage cutting element 116 between the retracted position (FIG. 5) and the activated position (FIG. 6). For example, cartilage cutting element 116 may be movably connected to apparatus base 292 in a manner that restricts the movement of cartilage cutting element 116 to parallel with cutting direction 288. Cutting element actuator 120 may be connected to cartilage cutting element 116 in any manner that allows cutting element actuator 120 to apply forces (directly or indirectly) to cartilage cutting element 116 to move cartilage cutting element 116 parallel to cutting direction 288 (e.g. towards the retracted position (FIG. 5) and/or towards the activated position (FIG. 5)).

Referring to FIGS. 13-14, in some embodiments, cartilage cutting element 116 may be coupled to apparatus base 292 by one or more guides, such as for example guide rods or tracks, which restrain the movement of cartilage cutting element 116 to cutting direction 288 (at least when moving from the retracted position (FIG. 5) to the activated position (FIG. 6)). The illustrated embodiment shows cartilage cutting element 116 coupled to apparatus base 292 by guide rods 296. As shown, guide rods 296 extend parallel to cutting direction 288. During a cutting operation, cartilage cutting element 116 may move along (e.g. slide along) guide rods 296 between the retracted position (FIG. 5) and the activated position (FIG. 6).

Cartilage cutting element 116 may be any member suitable for making precision cuts through a cartilage sample. For example, cartilage cutting element 116 may be a cutting blade (e.g. straight or serrated edged blade), a curved (e.g. circular) saw blade, or a thin wire.

Figure 15:
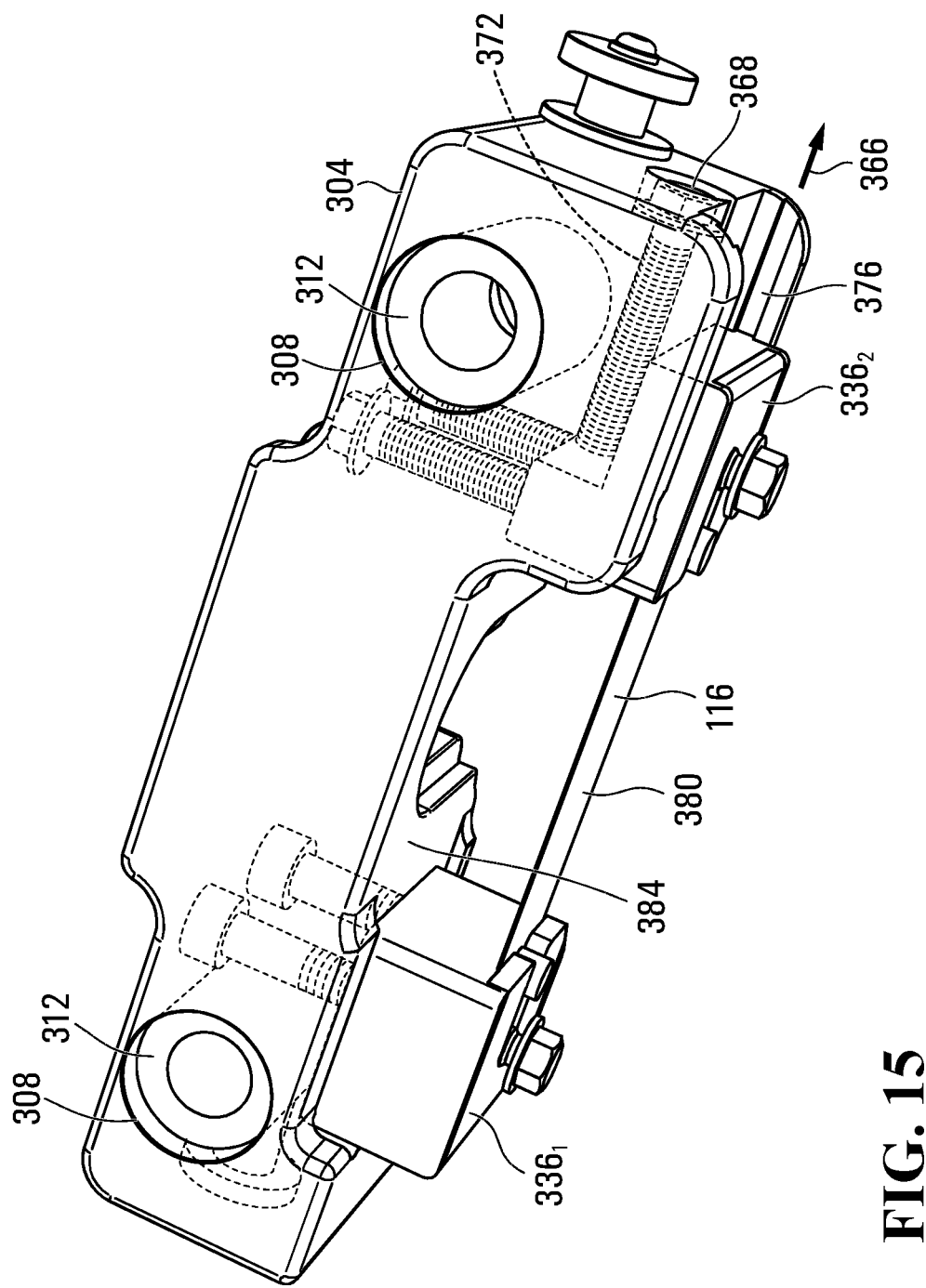
FIG. 15 is a top perspective view of the cutting block of the cartilage slicing apparatus of FIG. 1 in accordance with an embodiment.

Cartilage cutting element 116 may be coupled to a guide directly or indirectly. In the illustrated embodiment, cartilage cutting element 116 is shown indirectly coupled to guide rods 296 by a cutting block 304. As shown, cutting block 304 carries cartilage cutting element 116 (e.g. a cutting blade or thin wire), and is movably (e.g. slideably) mounted to guide rods 296. For example, cutting block 304 may have tracks 308 (e.g. bores) which mate with (e.g. receive) guide rods 296. As shown in FIG. 15, tracks 308 may include bearings 312 (e.g. roller bearings, ball bearings, or bushings). Returning to FIGS. 13-14, this may reduce friction between tracks 308 and guide rods 296.

Still referring to FIGS. 13-14, cutting element actuator 120 may be connected to cutting block 304 in a manner that allows cutting element actuator 120, when activated, to move cutting block 304 along guides 296. In one example, cutting element actuator 120 may include a handle rigidly connected to (e.g. integrally formed with) cutting block 304 whereby the user pushes upon the handle to move the handle and cutting block 304 together in the cutting direction 288. In other embodiments, cutting element actuator 120 is movably (e.g. pivotably and/or slideably) connected to cutting block 304 in a manner that provides mechanical advantage to the user. For example, when moving cutting element actuator 120 between the retracted position (FIG. 5) and the activated position (FIG. 6), handle 290 may travel a longer distance than cutting block 304. This reduces the force required to be applied to handle 290 as compared with applying force directly to cutting block 304 (e.g. in the case of a handle rigidly connected to cutting block 304).

As shown, handle 290 may be rotatably (e.g. pivotably) connected to apparatus base 292 by one or more lever arms 316. Lever arms 316 may have a proximal portion 320 (e.g. proximal end) rotatably connected to base 292, and a distal portion 324 (e.g. distal end) connected to handle 290. Lever arms 316 may be rotatably and/or slidably connected to cutting block 304 between lever arm proximal and distal portions 320, 324. This provides handle 290 a mechanical advantage over cutting block 304 when using handle 290 to rotate lever arms 316 about proximal portion 320 for moving cutting block 304 in cutting direction 288.

Optionally, lever arms 316 may extend non-linearly (e.g. curved or bent as shown) from lever arm proximal portion 320 to lever arm distal portion 324. For example, lever arms 316 may bend (e.g. curve) away from apparatus base 292 towards lever arm distal portion 324. This can provide handle 290, which is connected to lever arm distal portion 324, with a retracted position that avoid obstructing visibility and manual access to cartilage carrier 104 (FIG. 1).

Still referring to FIGS. 13-14, in some embodiment cutting element actuator 120 when moved to the retracted position, may remain in the retracted position without user assistance. For example, cartilage cutting assembly 108 may include a lock that holds cutting element actuator 120 in the retracted position. Alternatively or in addition to a lock, cutting element actuator 120 may be biased to the retracted position. Either way, this can allow cutting element actuator 120 to remain in the retracted position, without user assistance, while a cartilage sample is moved into position for slicing. In the illustrated embodiment, cutting element actuator 120 includes a bias 328 (e.g. coil spring as shown, torsional spring, leaf spring, or other resiliently deformable member) that urges (i.e. biases) cutting element actuator 120 towards the retracted position. In the example shown, bias 328 is a coil spring which surrounds guide rods 296, and which exerts a biasing force upon cutting block 304 in a bias direction opposite to cutting direction 288. As shown, bias 328 may be positioned between cutting block 304 and apparatus base 292.

In alternative embodiments, cutting element actuator 120 does not remain in the retracted position without user assistance. This may simplify the design of cutting element actuator 120, which may reduce manufacturing complexity and cost.

Cartilage cutting assembly 108 may limit the travel distance of cartilage cutting element 116 from the retracted position (FIG. 5) to the activated position (FIG. 6). For example, cartilage cutting element assembly 108 may include one or more depth stops 332 that inhibit movement of cartilage cutting element 116 in the cutting direction 288 beyond the activated position (FIG. 6). This may prevent cartilage cutting element 116 from cutting engagement with components of apparatus 100 (FIG. 1); such cutting engagements may damage or dull cartilage cutting element 116 and/or damage the engaged component. In the illustrated embodiment, cartilage cutting assembly 108 includes two depth stops 332 that are positioned between apparatus base 292 and cutting block 304, and that are aligned with cutting block 304 along an axis parallel to cutting direction 288. Cutting block 304 may contact depth stop 332 in the activated position, whereby depth stop 332 may inhibit further movement in cutting direction 288.

Figure 16:
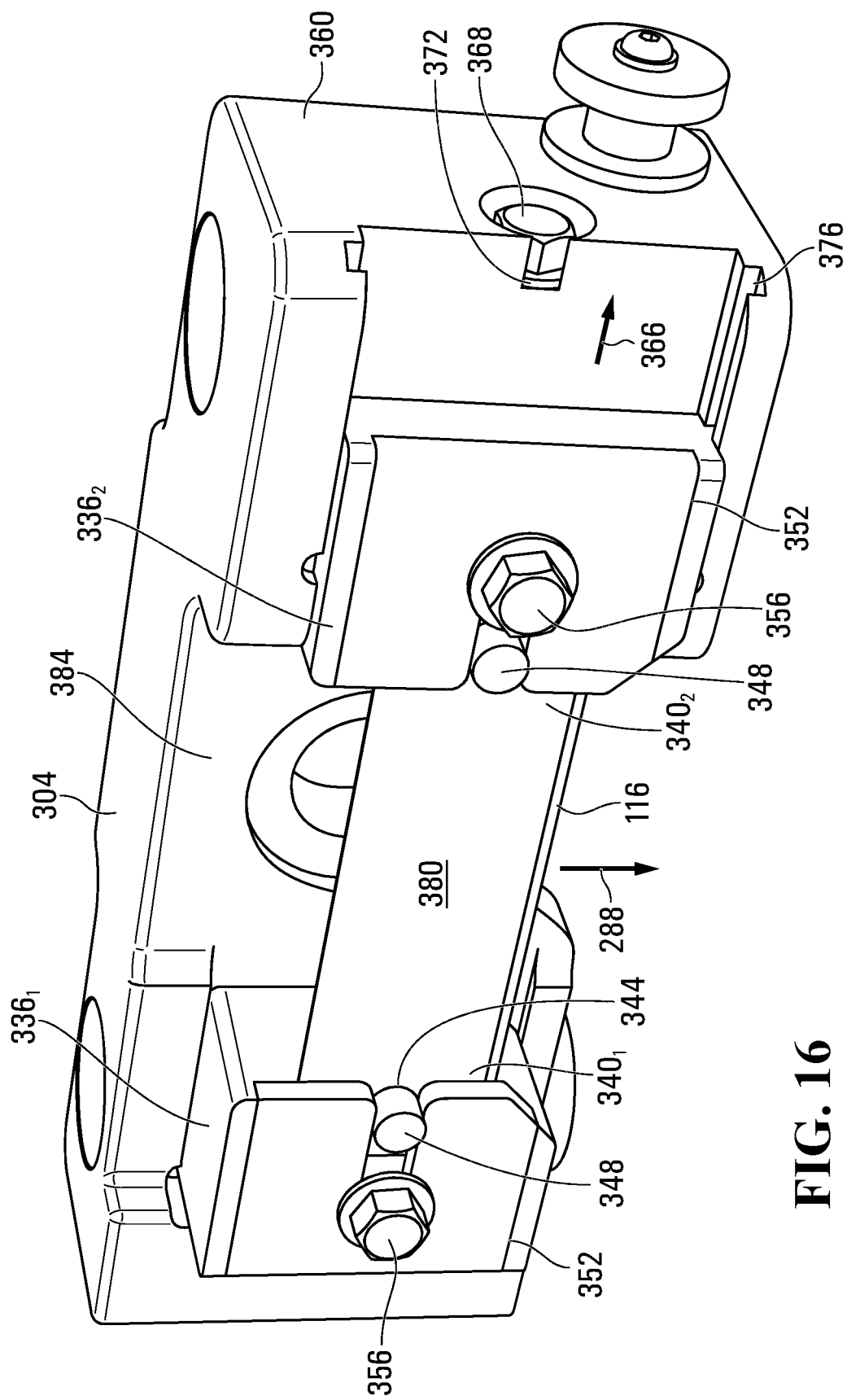
FIG. 16 is a rear perspective view of the cutting block of FIG. 15.
Figure 17:
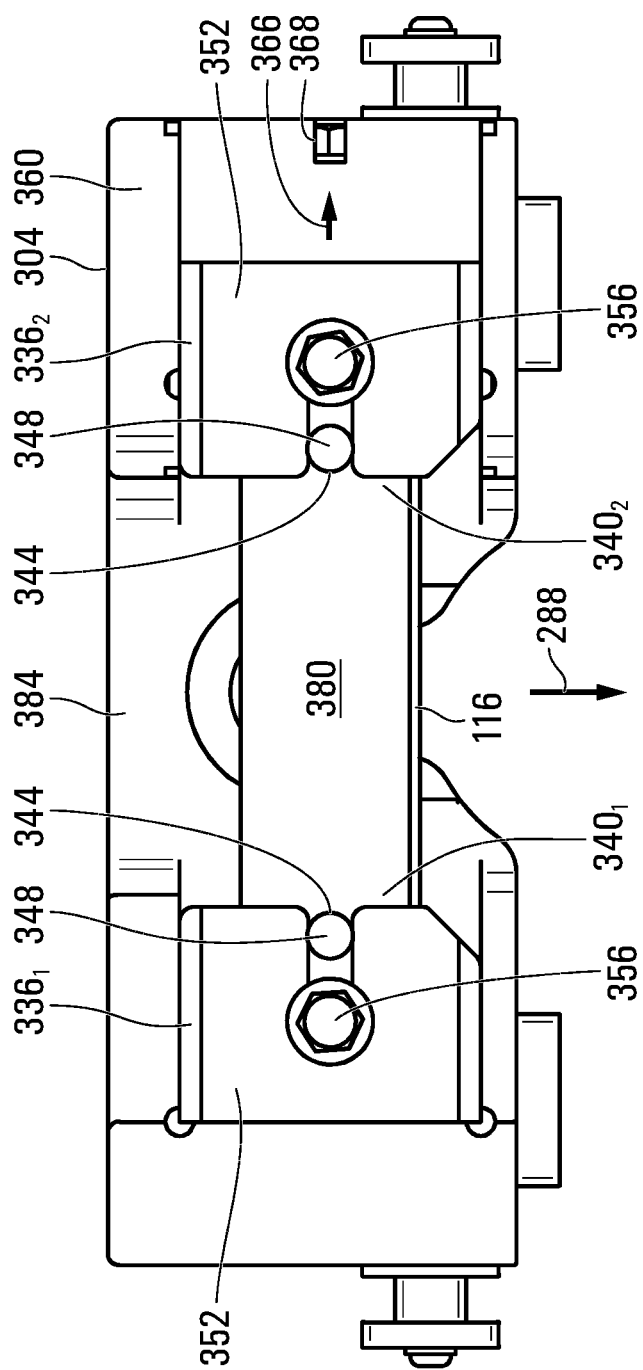
FIG. 17 is a rear elevation view of the cutting block of FIG. 15.

Reference is now made to FIGS. 16-17. Cutting block 304 may have any configuration suitable to hold cartilage cutting element 116 as cartilage cutting element 116 is moved across a cartilage sample to remove a cartilage sample slice. As described above, cutting block 304 may also accommodate a connection to cutting element actuator 120 (FIG. 13), which may be responsible for driving cutting block 304 to move in the cutting direction.

Cartilage cutting element 116 may be rigidly connected to cutting block 304. This can allow cartilage cutting element 116 and cutting block 304 to move together with constant relative orientation to each other during a cutting operation. This may contribute to a stable and repeatable cutting motion, all else being equal. Cartilage cutting element 116 may be permanently or removably connected to cutting block 304. A permanently connected (e.g. integrally formed) cartilage cutting element 116 may provide a more rigid, reliable, and stable connection between cartilage cutting element 116 and cutting block 304. However, if (or when) cartilage cutting element 116 becomes dull, it may require replacing the entire cutting block 304, leading to greater operating expense for apparatus 100 (FIG. 1).

In the example shown, cartilage cutting element 116 is removably connected to cutting block 304. Cartilage cutting element 116 may be removably connected to cutting block 304 in any manner that allows cartilage cutting element 116 (e.g. a cutting blade or cutting wire) to be removed for repair, sharpening, or replacement, and then reconnected to cutting block 304. As shown, first and second mounts 336 may removably join a respective lateral end 340 of cartilage cutting element 116 to cutting block 304. In the illustrated example, cartilage cutting element 116 is a cutting blade, and each lateral end 340 of cartilage cutting element 116 includes a mounting aperture 344 which receives a lug 348 of the respective mount 336. Each mount 336 is further shown including a retainer 352 that overlies the cutting blade 116 to keep the cutting blade 116 securely mounted to lugs 348. As shown, a removable bolt 356 secures the retainer 352 in place, whereby each lateral blade end 340 is sandwiched between the retainer 352 and the mount body 360. Bolts 356 and retainers 352 can be removed to allow blade 116 to dismount from lugs 348.

Figure 18:
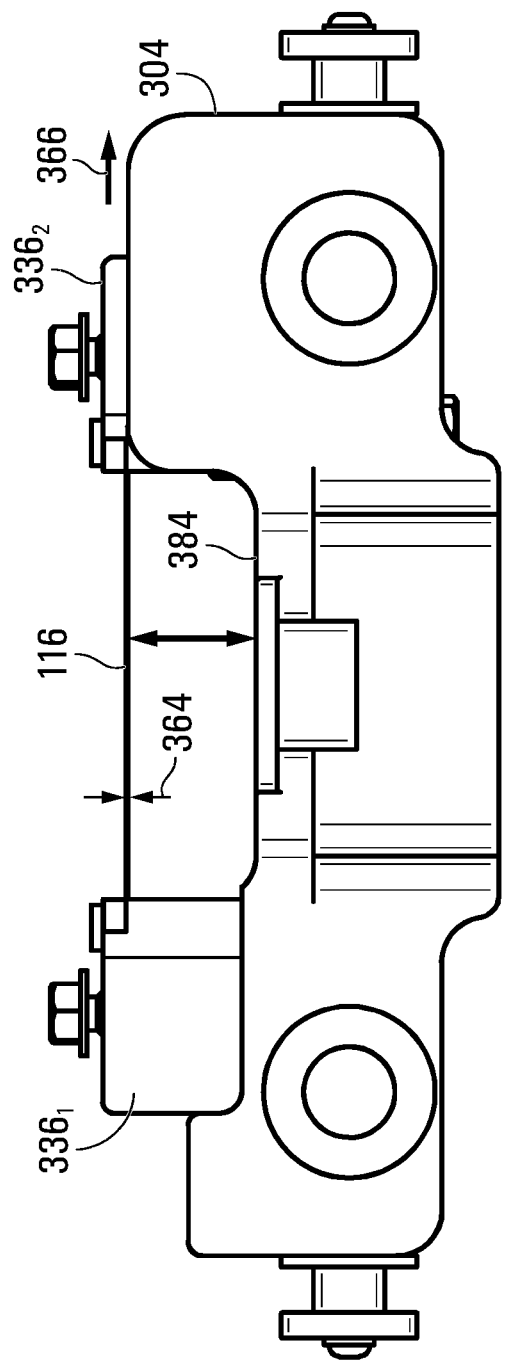
FIG. 18 is a bottom plan view of the cutting block of FIG. 15.

Referring to FIGS. 16-18, cartilage cutting element 116 may be thin to provide a sharp and clean cut. For example, cartilage cutting element 116 may have a thickness 364 of between 0.05 mm and 0.3 mm. Other thicknesses 364 are possible and may be desirable depending on the application. Generally, a large thickness 364 (e.g. greater than 0.3 mm) can provide a more robust cartilage cutting element 116 that is less prone to deflecting during a cutting operation, all else being equal. However, the thick cartilage cutting element 116 may tend to make cuts that are less even (e.g. more rough), e.g. because it behaves as a wedge that deforms the cartilage sample during cutting. This can result in a cartilage slice that has cut ends which are less planar than ideal. This may not be problematic for some applications.

On the other hand, a very small thickness 364 (e.g. in the range of 0.05 mm to 0.3 mm) may provide a very clean cut with minimal cartilage sample deflection during cutting. However, a thin cartilage cutting element 116 may have less structural rigidly and therefore tend to bend (i.e. deflect) during cutting due to the difficulty of cutting cartilage. In some embodiments, the tendency to deflect may be mitigated by a cartilage cutting assembly 108 (FIG. 1) that exerts tension upon the cartilage cutting element 116 in a direction transverse to (e.g. perpendicular to) the cutting direction 288. The tension may help to reduce deflection that cartilage cutting element 116 may experience during cutting operations. In some embodiments, the tension may be adjustable to accommodate for a variation in cartilage stiffness from sample to sample. For example, a cutting element 116 under high tension may deflect less, but may be more prone to breaking if the cartilage is too stiff. A user may adjust the tension to a setting that mitigates deflection without creating too great a risk of the blade breaking.

Cartilage cutting assembly 108 may be configured in any manner that allows it to exert tension upon cartilage cutting element 116 in a direction transverse to (e.g. perpendicular to) cutting direction 288. For example, at least one of cutting element mounts 336 may be movable relative to the other mount 336 in a tension direction 366 (also referred to as the transverse tension direction) that is transverse to (e.g. perpendicular to) cutting direction 288. In the illustrated embodiment, cutting element mount $336_1$ is rigidly connected to cutting block 304, and cutting element mount $336_1$ is movable in tension direction 366 relative to cutting element mount $336_2$ to exert tension upon the mounted cartilage cutting element 116. As shown, cutting block 304 may include a user-operable tension adjuster 368 for selectively increasing tension upon cutting element mount $336_2$. In use, tension adjuster 368 may be manually driven (e.g. by hand) or power driven (e.g. by an electromechanical device, such as a motor or solenoid) when activated to move cutting element mount $336_2$ in tension direction 366 away from cutting element mount $336_1$ and thereby increase tension upon cartilage cutting element 116.

As shown in FIGS. 15-16, tension adjuster 368 may include a threaded member 372 (e.g. bolt) that threadably engages cutting element mount $336_2$. When threaded member 372 is rotated (e.g. by hand or by powered means), cutting element mount $336_2$ may be threadably advanced in transverse tension direction 366. In the illustrated example, cutting element mount $336_2$ is movably connected to cutting block 304 in a manner that constrains cutting element mount $336_2$ to movement parallel to tension direction 366. For example, cutting element mount $336_2$ may be connected to cutting block 304 by a guide 376 (e.g. a track as shown) aligned parallel to tension direction 366.

In other embodiments, cartilage cutting assembly 108 (FIG. 13) is not configured to exert an adjustable tension upon cartilage cutting element 116. This may simplify the design of cartilage cutting assembly 108 (FIG. 13), which may reduce manufacturing complexity and cost.

Reference is now made to FIGS. 1 and 15-18. In some embodiments, cartilage cutting assembly 108 provides clearance behind cartilage cutting element 116 to accommodate (e.g. receive) front cartilage support 156. This allows cartilage cutting element 116 to move to the activated position (FIG. 6) without interference by front cartilage support 156. As shown, cutting block 304 may hold cartilage cutting element 116 with cutting element mid-section 380 longitudinally spaced from cutting block 304. This longitudinal spacing provides a volume to receive the cut cartilage slice and front cartilage support 156 when cartilage cutting element 116 is moved to the activated position (FIG. 6). As shown, cutting block 304 may include a rear surface 384 longitudinally aligned with cartilage cutting element 116, and which is spaced rearwardly from cutting element mid-section 380. Optionally, cutting block rear surface 384 may be recessed to accommodate, e.g. cartilage cutting element 116 and/or slice thickness adjuster 268 (if present).

Figure 19:
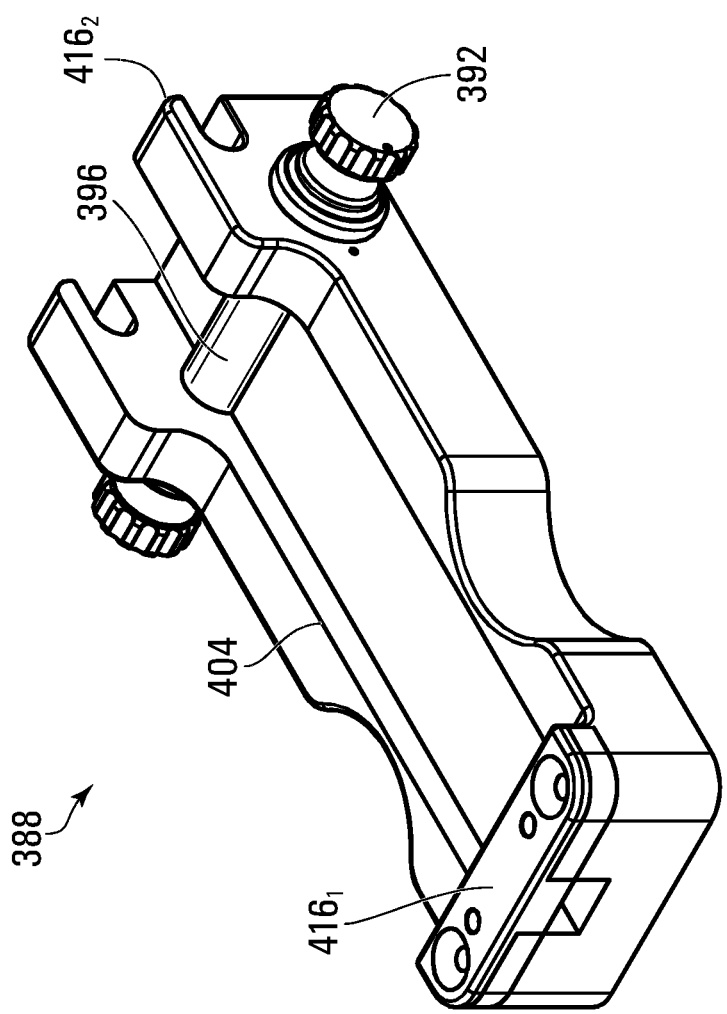
FIG. 19 is a perspective view of a carrier mount of the cartilage slicing apparatus of FIG. 1, with a carrier lock in a locked position, in accordance with an embodiment.
Figure 20:
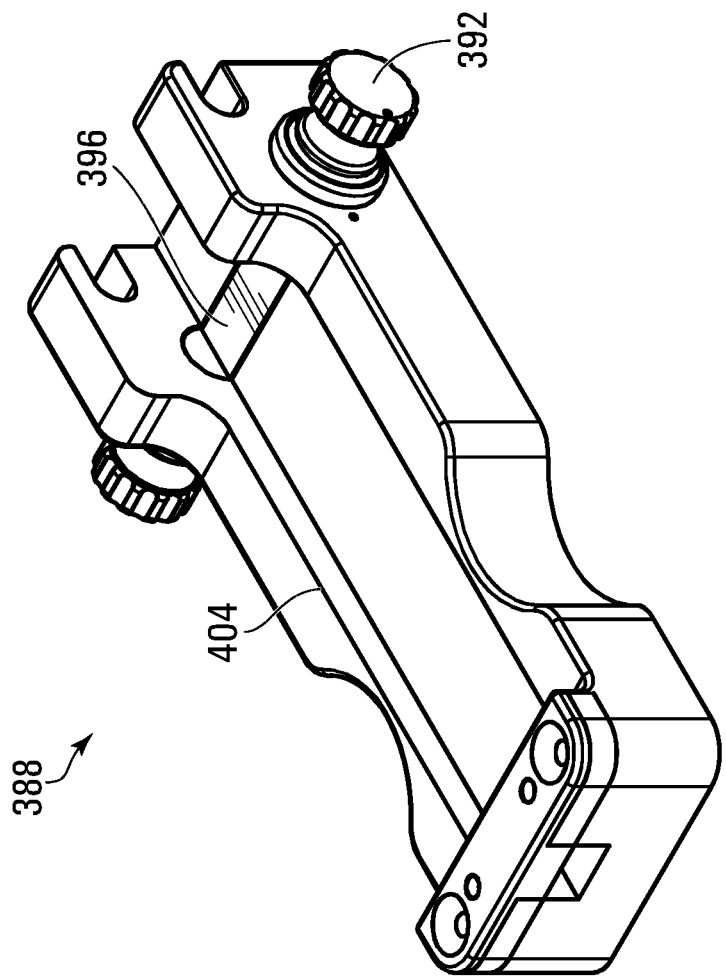
FIG. 20 is a perspective view of the carrier mount of FIG. 19 with the carrier lock in an unlocked position.

Reference is now made to FIGS. 1 and 19-20. Cartilage carrier 104 may be permanently or removably connected to apparatus base 292. A permanent connection may make apparatus 100 more robust, with fewer components, possibly simplifying the design and making it less expensive to manufacture. A removable connection may allow cartilage carrier 104 to be removed from apparatus base 292 (e.g. while cartilage cutting assembly 108 remains connected to apparatus base 292) to reposition a cartilage sample 112 in-situ, or to insert a new cartilage sample 112. Afterwards the cartilage carrier 104 may be reconnected to apparatus base 292.

As shown, apparatus base 292 may include a carrier mount 388. Carrier mount 388 may be rigidly connected (e.g. integrally formed) with apparatus base 292. Cartilage carrier 104 may be removably connected to apparatus base 292 by carrier mount 388. In some embodiments, carrier mount 388 includes a carrier lock 392 that is movable between a locked position (FIG. 19) and an unlocked position (FIG. 20). When cartilage carrier 104 is seated on carrier mount 388, and carrier mount 388 is in the locked position (FIGS. 1 and 19), carrier lock 392 inhibits cartilage carrier 104 from being removed from apparatus base 292.

When carrier mount 388 is in the unlocked position (FIG. 20), carrier lock 392 is disengaged from cartilage carrier 104, which may allow cartilage carrier 104 to be freely dismounted and remounted to apparatus base 292.

Referring to FIGS. 1, 8, and 19, carrier lock 392 may have any configuration that allows carrier lock 392 to prevent a mounted cartilage carrier 104 from being removed from apparatus base 292 when in the locked position. In the illustrated example, carrier lock 392 includes a semi-cylindrical dowel 396 that extends across a carrier recess 404. As shown, carrier lock dowel 396 may be rotatable between a locked position (FIG. 19), in which carrier lock dowel 396 protrudes into carrier recess 404 and mates with a locking recess 408 formed in cartilage carrier 104; and an unlocked position (FIG. 20), in which carrier lock dowel 396 is positioned outside of carrier recess 404 and locking recess 408 (e.g. is flush with carrier recess 404). When in the locked position (FIGS. 1 and 19), carrier lock 392 inhibits cartilage carrier 104 from being withdrawn rearwardly from carrier recess 404. As shown, cartilage carrier 104 may further include front and rear abutment members 412 (e.g. nose $412_1$ and post $412_2$) which sit under front and rear abutment members 416 of carrier mount 388 when cartilage carrier 104 is seated on carrier mount 388. In the illustrated example, front and rear abutment members 416 engage front and rear abutment members 412, respectively to inhibit cartilage carrier 104 from dismounting transversely (e.g. vertically as shown) from carrier mount 388. When carrier lock 392 is in the unlocked position, front and rear abutment members 412 may be withdrawn rearwardly from abutment members 416, thereby allowing cartilage carrier 104 to be dismounted from apparatus base 292.

In connection with any embodiment disclosed herein, one or more (or all) of the manual or power adjustable members may be operable to lock their position in place prior to a cutting operation. For example, knobs 180, 188, 244, and 276 (FIG. 7) may be configured to lock (e.g. tightened) so that they do not inadvertently turn and thereby loosen the engagement of the associated cartilage sample engaging member with the cartilage sample held by the apparatus.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

Items

Item 1: An apparatus for slicing a cartilage sample, the apparatus having a longitudinal axis extending in forward and rearward directions, the apparatus comprising:
a rear cartilage support cup;
a cartilage clamp positioned forward of the rear cartilage support cup,
the cartilage clamp having first and second clamp members, the first clamp member being spaced apart from and aligned with the second clamp member in a clamping direction transverse to the longitudinal axis, and at least one of the first and second clamp members being movable parallel to the clamping direction;

a front cartilage support, the front cartilage support positioned forward of the cartilage clamp;

a cartilage receiving region bounded by the first and second clamp members, the front cartilage support, and the rear cartilage support cup; and a cartilage cutting element positioned forward of the cartilage clamp, the cartilage cutting element spaced rearwardly from the front cartilage support by a cartilage slice thickness, the cartilage cutting element being movable across the cartilage receiving region in a cutting direction transverse to the longitudinal axis.

Item 2: The apparatus of any preceding item, further comprising a cutting element tensioner coupled to the cartilage cutting element, and user operable to increase tension upon the cartilage cutting element in a tension direction transverse to both the longitudinal axis and the cutting direction.

Item 3: The apparatus of any preceding item, wherein both of the first and second clamp members are selectively movable parallel to the clamping direction relative to each other.

Item 4: The apparatus of any preceding item, further comprising a handle coupled to the cartilage cutting element, the handle being manually user operable to move the cartilage cutting element across the cartilage receiving region in the cutting direction.

Item 5: The apparatus of any preceding item, wherein at least one of the first and second clamp members comprises a cartilage contacting surface having a plurality of ridges.

Item 6: The apparatus of any preceding item, wherein the cartilage support cup is selectively movable longitudinally relative to the front cartilage support.

Item 7: The apparatus of any preceding item, wherein the cartilage support cup is also movable in one or more directions transverse to the longitudinal axis.

Item 8: The apparatus of any preceding item, wherein the cartilage support cup is rotatable about a rotation axis transverse to the longitudinal axis.

Item 9: The apparatus of any preceding item, further comprising a slice thickness adjuster, the slice thickness adjuster comprising: the front cartilage support and a slice thickness selector that is user-operable to move the front cartilage support longitudinally relative to the cartilage cutting element.

Item 10: The apparatus of any preceding item, wherein the slice thickness selector comprises a manually user-operable adjustment dial.

Item 11: The apparatus of any preceding item, wherein the adjustment dial and the front cartilage support are coupled by threads, whereby rotating the adjustment dial moves the front cartilage support longitudinally relative to the cartilage cutting element.

Item 12: The apparatus of any preceding item, wherein the adjustment dial comprises at least one visual slice thickness indicium indicative of the cartilage slice thickness.

Item 13: The apparatus of any preceding item, further comprising an apparatus base, wherein each of the rear cartilage support cup, the cartilage clamp, the front cartilage support, and the cartilage cutting element is coupled to the apparatus base.

Item 14: The apparatus of any preceding item, further comprising:

a cartilage carrier, the cartilage carrier including the rear cartilage support cup, the cartilage clamp, and the front cartilage support, wherein the cartilage carrier is removable from the apparatus base as a unitary assembly while the cartilage cutting element remains connected to the apparatus base.

Item 15: The apparatus of any preceding item, wherein the apparatus base has a carrier recess, and the cartilage carrier is seated in the carrier recess when connected to the base.

Item 16: The apparatus of any preceding item, further comprising a carrier lock movable between a locked position in which the carrier lock inhibits the cartilage carrier from being removed from the apparatus base, and an unlocked position in which the carrier lock is disengaged from the cartilage carrier.

Item 17: A method of cutting a cartilage sample, the method comprising:

moving a front cartilage support longitudinally relative to a cartilage cutting element to define a slice thickness, the slice thickness measured in a forward direction;

immobilizing the cartilage sample by engaging the cartilage sample with a transverse cartilage clamp, a rear cartilage support cup, and the front cartilage support; and cutting, with the cartilage cutting element, in a cutting direction that is transverse to the forward direction, a cartilage slice of the immobilized cartilage sample, the cartilage slice having a front end in contact with the front cartilage support and having the slice thickness.

Item 18: The method of any preceding item, wherein said cutting comprises moving a handle to drive the cartilage cutting element through the immobilized cartilage sample.

Item 19: The method of any preceding item, wherein said immobilizing comprises:

moving at least one of first and second clamp members of the cartilage clamp in a clamping direction transverse to the forward direction to clamp transversely opposed sides of the cartilage sample; and moving the rear cartilage support cup so that the rear cartilage support cup and the front cartilage support make contact with opposed rear and front ends of the cartilage sample respectively.

Item 20: The method of any preceding item, wherein said immobilizing further comprises:

rotating the rear cartilage support cup about a rotation axis transverse to the forward direction to receive the rear end of the cartilage sample in a concave cartilage contacting surface of the rear cartilage support cup.

Item 21: The method of any preceding item, further comprising:

prior to said cutting, applying tension to the cartilage cutting element in a direction transverse to the cutting direction.

The invention claimed is:

1. An apparatus for slicing a cartilage sample, the apparatus having a longitudinal axis extending in forward and rearward directions, the apparatus comprising:

a rear cartilage support cup;

a cartilage clamp positioned forward of the rear cartilage support cup, the cartilage clamp having first and second clamp members, the first clamp member being spaced apart from and aligned with the second clamp member in a clamping direction transverse to the longitudinal axis, and at least one of the first and second clamp members being movable parallel to the clamping direction;
a front cartilage support, the front cartilage support positioned forward of the cartilage clamp;
a cartilage receiving region bounded by the first and second clamp members, the front cartilage support, and the rear cartilage support cup; and
a cartilage cutting element positioned forward of the cartilage clamp, the cartilage cutting element spaced rearwardly from the front cartilage support by a cartilage slice thickness, the cartilage cutting element being movable across the cartilage receiving region in a cutting direction transverse to the longitudinal axis.

2. The apparatus of claim 1, further comprising a cutting element tensioner coupled to the cartilage cutting element, and user operable to increase tension upon the cartilage cutting element in a tension direction transverse to both the longitudinal axis and the cutting direction.

3. The apparatus of claim 1, wherein both of the first and second clamp members are selectively movable parallel to the clamping direction relative to each other.

4. The apparatus of claim 1, further comprising a handle coupled to the cartilage cutting element, the handle being manually user operable to move the cartilage cutting element across the cartilage receiving region in the cutting direction.

5. The apparatus of claim 1, wherein at least one of the first and second clamp members comprises a cartilage contacting surface having a plurality of ridges.

6. The apparatus of claim 1, wherein the cartilage support cup is selectively movable longitudinally relative to the front cartilage support.

7. The apparatus of claim 6, wherein the cartilage support cup is also movable in one or more directions transverse to the longitudinal axis.

8. The apparatus of claim 1, wherein the cartilage support cup is rotatable about a rotation axis transverse to the longitudinal axis.

9. The apparatus of claim 1, further comprising a slice thickness adjuster, the slice thickness adjuster comprising: the front cartilage support and a slice thickness selector that is user-operable to move the front cartilage support longitudinally relative to the cartilage cutting element.

10. The apparatus of claim 9, wherein the slice thickness selector comprises a manually user-operable adjustment dial.

11. The apparatus of claim 10, wherein the adjustment dial and the front cartilage support are coupled by threads, whereby rotating the adjustment dial moves the front cartilage support longitudinally relative to the cartilage cutting element.

12. The apparatus of claim 10, wherein the adjustment dial comprises at least one visual slice thickness indicium indicative of the cartilage slice thickness.

13. The apparatus of claim 1, further comprising an apparatus base, wherein each of the rear cartilage support cup, the cartilage clamp, the front cartilage support, and the cartilage cutting element is coupled to the apparatus base.

14. The apparatus of claim 13, further comprising:
a cartilage carrier, the cartilage carrier including the rear cartilage support cup, the cartilage clamp, and the front cartilage support,
wherein the cartilage carrier is removable from the apparatus base as a unitary assembly while the cartilage cutting element remains connected to the apparatus base.

15. The apparatus of claim 14, wherein the apparatus base has a carrier recess, and the cartilage carrier is seated in the carrier recess when connected to the base.

16. The apparatus of claim 14, further comprising a carrier lock movable between a locked position in which the carrier lock inhibits the cartilage carrier from being removed from the apparatus base, and an unlocked position in which the carrier lock is disengaged from the cartilage carrier.

17. A method of cutting a cartilage sample, the method comprising:
moving a front cartilage support longitudinally relative to a cartilage cutting element along a longitudinal axis extending in forward and rearward directions to define a slice thickness, the slice thickness measured in the forward direction;
immobilizing the cartilage sample by engaging the cartilage sample with a transverse cartilage clamp, a rear cartilage support cup, and the front cartilage support; and
cutting, with the cartilage cutting element, in a cutting direction that is transverse to the forward direction, a cartilage slice of the immobilized cartilage sample, the cartilage slice having a front end in contact with the front cartilage support and having the slice thickness.

18. The method of claim 17, wherein said cutting comprises moving a handle to drive the cartilage cutting element through the immobilized cartilage sample.

19. The method of claim 17, wherein said immobilizing comprises:
moving at least one of first and second clamp members of the cartilage clamp in a clamping direction transverse to the forward direction to clamp transversely opposed sides of the cartilage sample; and
moving the rear cartilage support cup so that the rear cartilage support cup and the front cartilage support make contact with opposed rear and front ends of the cartilage sample respectively.

20. The method of claim 17, further comprising:
prior to said cutting, applying tension to the cartilage cutting element in a direction transverse to the cutting direction.

* * * * *